(12) United States Patent
Maggio et al.

(10) Patent No.: US 8,329,220 B2
(45) Date of Patent: Dec. 11, 2012

(54) CONTROLLED RELEASE FORMULATIONS

(75) Inventors: Edward T. Maggio, San Diego, CA (US); Elias Meezan, Birmingham, AL (US); Dennis J. Pillion, Hoover, AL (US); Sarah L. Morgan, Hoewood, AL (US); Joe Baggott, Mountain Brook, AL (US)

(73) Assignees: Aegis Therapeutics, LLC, San Diego, CA (US); The UAB Research Foundation, Birmingham, AL (US)

( * ) Notice: Subject to any disclaimer, the term of this patent is extended or adjusted under 35 U.S.C. 154(b) by 461 days.

(21) Appl. No.: 12/197,179

(22) Filed: Aug. 22, 2008

(65) Prior Publication Data

US 2009/0110735 A1 Apr. 30, 2009

Related U.S. Application Data

(60) Provisional application No. 60/957,960, filed on Aug. 24, 2007, provisional application No. 61/086,743, filed on Aug. 6, 2008, provisional application No. 61/188,441, filed on Aug. 7, 2008.

(51) Int. Cl.
*A61K 9/10* (2006.01)
*A61K 31/519* (2006.01)
*A61K 31/12* (2006.01)
*A61K 38/02* (2006.01)
*A61K 31/122* (2006.01)
*A61K 31/56* (2006.01)
*A61K 38/22* (2006.01)
*A61P 19/02* (2006.01)
*A61P 25/28* (2006.01)

(52) U.S. Cl. ........ 424/488; 424/94.1; 424/484; 514/1.1; 514/178; 514/252.16; 514/262.1; 514/685

(58) Field of Classification Search .................. None
See application file for complete search history.

(56) References Cited

U.S. PATENT DOCUMENTS

| | | | |
|---|---|---|---|
| 5,369,095 A * | 11/1994 | Kee et al. ................ 514/24 |
| 5,661,130 A | 8/1997 | Meezan et al. |
| 6,365,185 B1 | 4/2002 | Ritschel et al. ............. 424/473 |
| 7,048,946 B1 | 5/2006 | Wong et al. ................. 424/486 |
| 2002/0058066 A1 * | 5/2002 | Tomohira et al. ............ 424/480 |
| 2003/0049311 A1 * | 3/2003 | McAllister et al. ........... 424/452 |
| 2005/0208095 A1 | 9/2005 | Hunter et al. ............... 424/423 |
| 2006/0046962 A1 | 3/2006 | Meezan et al. ............... 514/12 |
| 2006/0052478 A1 * | 3/2006 | Madsen et al. .............. 523/106 |
| 2006/0159766 A1 * | 7/2006 | Jenkins et al. .............. 424/489 |

OTHER PUBLICATIONS

An et al. (Drug Development and Industrial Pharmacy vol. 29, No. 1, pp. 99-105, 2003).*
Szuts et al. (Intl. Journ. Pharmaceutics 383 (2010 132-137).*

* cited by examiner

*Primary Examiner* — David J Blanchard
*Assistant Examiner* — Garen Gotfredson

(57) ABSTRACT

The present invention provides stable, self-assembling, biocompatible and biodegradable hydrogel formulations, into which one or more compounds may be incorporated allowing for delayed release or controlled release of the incorporated compounds as the hydrogel is degraded in the body.

12 Claims, 37 Drawing Sheets

CONTROLLED RELEASE FORMULATIONS

CROSS REFERENCE TO RELATED APPLICATION(S)

This application claims the benefit of priority under 35 U.S.C. §119(e) of U.S. Ser. No. 60/957,960, filed Aug. 24, 2007; the benefit of priority under 35 U.S.C. §119(e) of U.S. Application Ser. No. 61/086,743, filed Aug. 6, 2008; and the benefit of priority under 35 USC §119(e) of U.S. Application Ser. No. 61/188,441, filed Aug. 7, 2008. The disclosure of each of the prior applications is considered part of and is incorporated by reference in the disclosure of this application

BACKGROUND OF THE INVENTION

1. Field of the Invention

The invention relates generally to controlled release formulations and more specifically to the use of hydrogels for delivery of therapeutic agents to subjects in need thereof.

2. Background Information

Hydrogels are materials that absorb solvents (such as water), undergo rapid swelling without discernible dissolution, and maintain three-dimensional networks capable of reversible deformation. Hydrogels may be uncrosslinked or crosslinked. Uncrosslinked hydrogels are able to absorb water but do not dissolve due to the presence of hydrophobic and hydrophilic regions. Covalently crosslinked networks of hydrophilic polymers, including water soluble polymers, are traditionally denoted as hydrogels when in the hydrated state. A number of aqueous hydrogels have been used in various biomedical applications, such as, for example, soft contact lenses, wound management, and drug delivery.

Hydrogels can be formed from natural polymers such as glycosaminoglycans and polysaccharides, proteins, etc., where the term "glycosaminoglycan" encompasses complex polysaccharides that are not biologically active (for example, not compounds such as ligands or proteins) and have repeating units of either the same saccharide subunit or two different saccharide subunits. The hydrogels most often cited in the literature are those made of water soluble polymers, such as polyvinyl pyrrolidone, which have been crosslinked with naturally derived biodegradable components such as those based on albumin. Another known substance for forming hydrogels, also known as a gelator, is amygdalin hydrogelators which are made by chemically modifying the naturally occurring glycoside amygdalin. Amygdalin may be found in apple, almond, peach, cherry and apricot pits and gels formed from these molecules are potentially toxic when degraded in the body. The production of amygdalin hydrogelators requires synthetic modification of the parent compound amygdalin to produce products capable of gelation Totally synthetic hydrogels that have been studied for controlled drug release, and as membranes for the treatment of post-surgical adhesion, are based on covalent networks formed by the addition polymerization of acrylic-terminated, water soluble chains of polyether dipolylactide block copolymers.

Many hydrogels are currently in use for drug delivery to a subject despite significant limitations, such as the need for chemical modification to produce substances suitable to form hydrogels and the inability of specific gelators to form hydrogels capable of incorporating therapeutic agents of widely varying solubility.

SUMMARY OF THE INVENTION

The invention provides controlled release formulations that are able to predictably release therapeutic agents into subjects in need thereof. In one embodiment, a controlled release formulation is provided that includes a therapeutic agent entrapped in an alkyglycoside biodegradable hydrogel, such a tetradecylmaltoside hydrogel. In another embodiment, the invention provides a controlled release formulation comprising a therapeutic agent entrapped in a sucrose ester biodegradable hydrogel. In another embodiment, the invention provides a controlled release bilayer formulation comprising a first layer and a second layer, wherein the first layer comprises a first therapeutic agent entrapped in an alkyglycoside biodegradable hydrogel, and the second layer comprises a second therapeutic agent entrapped in a sucrose ester biodegradable hydrogel. In another embodiment, the invention provides a controlled release bilayer formulation comprising a first layer and a second layer, wherein the first layer comprises a first therapeutic agent entrapped in a tetradecylmaltoside biodegradable hydrogel, and the second layer comprises a second therapeutic agent entrapped in a sucrose stearate biodegradable hydrogel.

In another aspect, the invention provides a method of treating rheumatoid arthritis. The method includes administering to a subject in need thereof a therapeutically effective amount of a controlled release bilayer formulation. In one embodiment, the formulation includes a first layer and a second layer, wherein the first layer comprises methotrexate entrapped in a tetradecylmaltoside biodegradable hydrogel, and the second layer comprises folic acid entrapped in a sucrose stearate biodegradable hydrogel.

In another aspect, a controlled release formulation is provided that includes an acetate buffered hydrogel including an alkylglycoside or sucrose ester, a therapeutic agent, and an acetate buffer. In one embodiment, the hydrogel may further include a preservative. Exemplary preservatives include ethylene diamine tetraacetic acid (EDTA), benzalkonium chloride, and sodium azide or dodecyl maltoside. Additionally, the acetate buffered hydrogel preferably has a pH from about 4 to 8 and more preferably from about 4.5 to 6.5.

In another aspect, the invention provides a method for transdermal delivery of a therapeutic agent to a subject using a controlled release formulation including an acetate buffered hydrogel. The method includes applying to the epidermis of the subject a composition including a therapeutic agent, an alkyglycoside or sucrose ester, and an acetate buffer.

In another aspect, the invention provides a method for increasing the residency time of a therapeutic agent during intranasal or pulmonary delivery of the agent to a subject using a controlled release formulation including an acetate buffered hydrogel. The method comprises applying to the nasal or pulmonary mucosa of the subject a composition including a therapeutic agent, an alkylglycoside or sucrose ester, and an acetate buffer, thereby increasing the residency time of the therapeutic agent in the nasal or pulmonary mucosa.

In various aspects, exemplary alkyglycosides and sucrose esters include, but are not limited to tetradecylmaltoside, sucrose stearate, sucrose distearate or a combination thereof.

In various aspects, exemplary therapeutic agents of the present invention include, but are not limited to organic molecules, peptides, steroids, hormones, anti-inflammatory agents, anti-biotics, anti-viral agents, Uv blockers, and anti-wrinkle agents. Exemplary anti-wrinkle agents include retinol, 13-trans retinoic acid, 13-cis retinoic acid, retinyl ester, hydroxy acid, alpha hydroxy acid, beta hydroxy acid, poly hydroxy acid, an exfoliant, a Coenzyme Q10 copper peptide, kinetin, tea extract (black, green, oolong, and the like) and a collagen. In other embodiments, exemplary therapeutic agents include methotrexate, folic acid, curcumin and combinations thereof. In yet other embodiments, the controlled release formulation comprises one or more of the above-disclosed therapeutic agents.

DETAILED DESCRIPTION OF THE INVENTION

Figure 1:
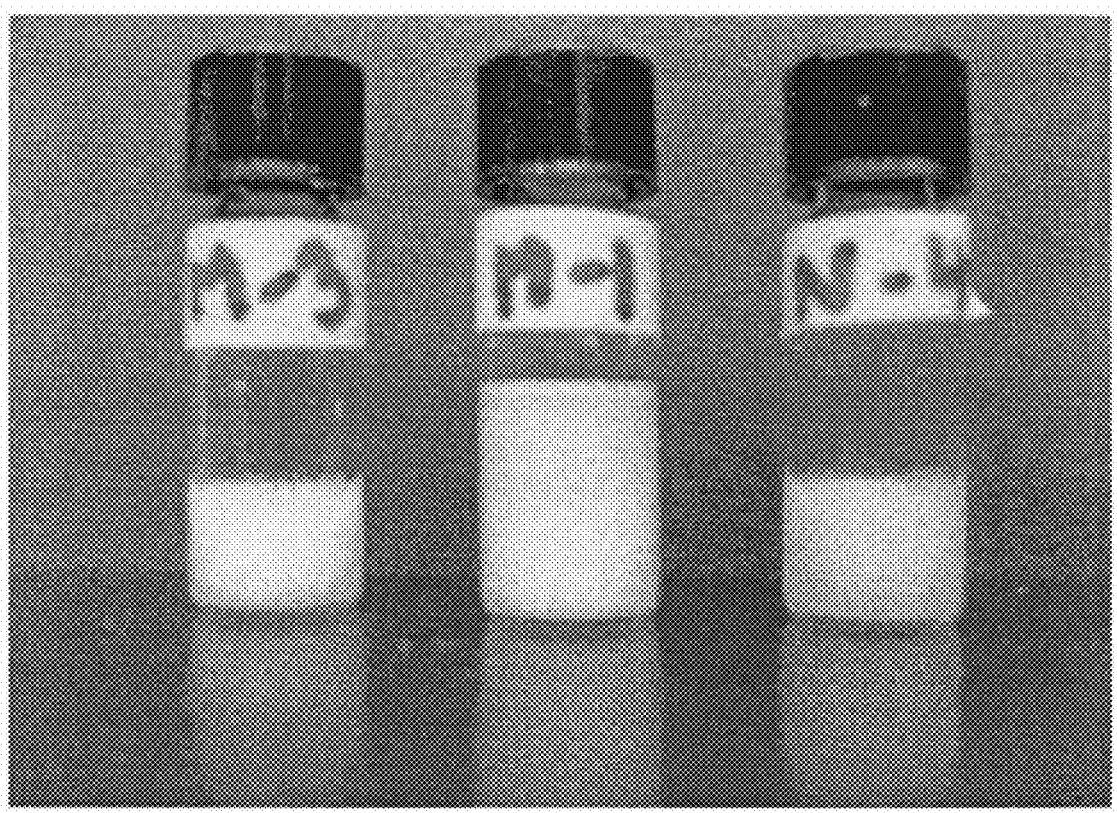
FIG. 1 is a pictorial representation showing hydrogels of folate and methotrexate. Sample M-3 is a hydrogel composed of 2% tetradecylmaltoside and 2.5 mg/ml methotrexate. Sample N-4 is a hydrogel composed of 2% sucrose stearate/distearate and 2.5 mg/ml folic acid. Sample M-1 is a bilayer hydrogel composed of 2% tetradecylmaltoside/2.5 mg/ml methotrexate in the bottom layer and 2% sucrose stearate/distearate/2.5 mg/ml folic acid in the top layer.

The present invention provides stable, self-assembling, biocompatible and biodegradable hydrogel formulations, into which one or more therapeutic agents may be incorporated allowing for delayed release or controlled release of the incorporated agents.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", an and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention provides improved hydrogel formulations which exhibit exceptional sustained and/or delayed release of a therapeutic agent. While the terms "therapeutic agent" and "drug" are intended to be synonymous, a therapeutic agent of the present invention may generally refer to any type of molecule, including but not limited to polynucleotides such as DNA, RNA, RNAi and antisense oligonucleotides; peptides such as a synthetic or naturally derived proteins, antibodies, and peptide hormones; steroids; peptidomimetics; peptoids such as vinylogous peptoids; chemical compounds such as organic molecules or small organic molecules; and the like.

Hydrogels are compositions comprised of molecules which are capable of gelling water or mixtures of water with other solvents to achieve a state of gelation, which is a delicate balance between solubility and precipitation. As used herein, a hydrogel is intended to include colloid gels or mixtures in which particles of one substance are distributed evenly throughout another substance. In the process of forming the hydrogel the gelators form a three dimensional matrix capable of trapping molecules, such as water and therapeutic agents, which are dissolved or suspended in the aqueous solution, into the gel. As used herein, the term "gelator" refers to any substance capable of forming a gel.

The present invention is based in part on the discovery that representatives of two classes of nonionic surfactant molecules, the alkylglycosides and the sucrose esters of long chain fatty acids are capable of self-assembly to form hydrogels with distinct properties into which a therapeutic agent may be encapsulated, producing formulations which allow for the controlled release of these agents.

As used herein, "alkylglycoside" refers to any sugar joined by a linkage to any hydrophobic alkyl, as is known in the art. Preferably the alkylglycoside is nonionic as well as nontoxic. Alkylglycosides are available from a number of commercial sources and may be natural or synthesized by known procedures, such as chemically or enzymatically.

In various aspects, alkylglycosides of the present invention may include, but not limited to: alkylglycosides, such as octyl-, nonyl-, decyl-, undecyl-, dodecyl-, tridecyl-, tetradecyl-, pentadecyl-, hexadecyl-, heptadecyl-, and octadecyl-α- or β-D-maltoside, -glucoside or -sucroside; alkyl thiomaltosides, such as heptyl, octyl, dodecyl-, tridecyl-, and tetradecyl-β-D-thiomaltoside; alkyl thioglucosides, such as heptyl- or octyl 1-thio α- or β-D-glucopyranoside; alkyl thiosucroses; alkyl maltotriosides; long chain aliphatic carbonic acid amides of sucrose β-amino-alkyl ethers; derivatives of palatinose and isomaltamine linked by amide linkage to an alkyl chain; derivatives of isomaltamine linked by urea to an alkyl chain; long chain aliphatic carbonic acid ureides of sucrose β-amino-alkyl ethers; and long chain aliphatic carbonic acid amides of sucrose β-amino-alkyl ethers.

As described above, the hydrophobic alkyl can thus be chosen of any desired size, depending on the hydrophobicity desired and the hydrophilicity of the saccharide moiety. For example, one preferred range of alkyl chains is from about 9 to about 24 carbon atoms. An even more preferred range is from about 9 to about 16 or about 14 carbon atoms. Similarly, some preferred glycosides include maltose, sucrose, and glucose linked by glycosidic linkage to an alkyl chain of 9, 10, 12, 13, 14, 16, 18, 20, 22, or 24 carbon atoms, e.g., nonyl-, decyl-, dodecyl- and tetradecyl sucroside, glucoside, and maltoside, etc. These compositions are nontoxic, since they are degraded to an alcohol or fatty acid and an oligosaccharide, and amphipathic. Additionally, the linkage between the hydrophobic alkyl group and the hydrophilic saccharide can include, among other possibilities, a glycosidic, thioglycosidic, amide, ureide, or ester linkage.

The gelators of the invention include a saccharide, such as glucose or sucrose. As use herein, a "saccharide" is inclusive of monosaccharides, oligosaccharides or polysaccharides in straight chain or ring forms, or a combination thereof to form a saccharide chain. Oligosaccharides are saccharides having two or more monosaccharide residues. Accordingly, examples of saccharides include glucose, maltose, maltotriose, maltotetraose, sucrose and trehalose.

In one aspect, an exemplary gelator is an alkylglycoside, such as alkylmaltoside. Alkylmaltosides are glycosides of the disaccharide maltose and alcohols. Typical alkylmaltosides are dodecylmaltoside, tetradecylmaltoside and hexadecylmaltoside which consist of a 12, 14 and 16 carbon straight chain alcohol respectively, glycosidically attached to maltose. In an exemplary embodiment, the alkylglycoside is tetradecylmaltoside.

In sugar chemistry, an anomer is either of a pair of cyclic stereoisomers (designated α or β of a sugar or glycoside, differing only in configuration at the hemiacetal (or hemiketal) carbon, also called the anomeric carbon or reducing carbon. If the structure is analogous to one with the hydroxyl group on the anomeric carbon in the axial position of glucose, then the sugar is an alpha anomer. If, however, that hydroxyl is equatorial, the sugar is a beta anomer. For example, α-D-glucopyranose and β-D-glucopyranose, the two cyclic forms of glucose, are anomers. Likewise, alkylglycosides occur as anomers. For example, dodecyl β-D-maltoside and dodecyl α-D-maltoside are two cyclic forms of dodecyl maltoside. The two different anomers are two distinct chemical structures, and thus have different physical and chemical properties. In one aspect of the invention, the alkylglycoside of the present invention is a β anomer. In an exemplary aspect, the alkylglycoside is a β anomer of an alkylmaltoside, such as tetradecyl-β-D-maltoside (TDM).

Thus, in one aspect of the present invention, the alkylglycoside used is a substantially pure alkylglycoside. As used herein a "substantially pure" alkylglycoside refers to one anomeric form of the alkylglycoside (either the α or β anomeric forms) with less than about 2% of the other anomeric form, preferably less than about 1.5% of the other anomeric form, and more preferably less than about 1% of the other anomeric form. In one aspect, a substantially pure alkylgycoside contains greater than 98% of either the α or β anomer. In another aspect, a substantially pure alkylgycoside contains greater than 99% of either the α or β anomer. In another aspect, a substantially pure alkylgycoside contains greater than 99.5% of either the α or β anomer. In another aspect, a substantially pure alkylgycoside contains greater than 99.9% of either the α or β anomer.

In another aspect of the invention, the gelator of the invention may include one or more sucrose esters. As used herein, "sucrose esters" are sucrose esters of fatty acids and is a complex of sucrose and fatty acid. Sucrose esters of long chain fatty acids are emulsifiers/surfactants in which one or more fatty acids are joined in ester linkage to the free hydroxyl groups of the disaccharide sucrose. Sucrose esters can take many forms because of the eight hydroxyl groups in sucrose available for reaction and the many fatty acid groups, from acetate on up to larger, more bulky fatty acids that can be reacted with sucrose. They are biodegradable, non-toxic and mild to the skin.

Accordingly, in one aspect, the gelator is a sucrose ester, such as a sucrose ester of the long chain fatty acid stearic acid. In an exemplary aspect, the gelator is a mixture of different sucrose esters of the long chain fatty acid stearic acid, such as sucrose monostearate and sucrose distearate. In various aspects, sucrose monostearate and sucrose distearate may be used alone or in combination at various concentration ratios. An exemplary mixture of sucrose monostearate and sucrose distearate is available commercially from Croda Inc. as Crodesta F-110®.

The present invention is based, in part, on the seminal discovery that alkylglycosides and sucrose esters are capable of forming stable hydrogels by self-assembly of the unmodified parent monomers. The ability of these substances to self-assemble into stable gels at or below room temperature, or after being heated to 37-45 degrees C., allows the incorporation of therapeutic agents into the gel matrix without chemical modification, so that upon release they are immediately available for absorption. Furthermore, the hydrogels are suited for various types of delivery systems. For example, due in part to exemplary stability and sustained release characteristics, the hydrogels of the present invention, particularly the acetate buffered hydrogels described herein, are suitable for transdermal and pulmonary delivery routes. The gelators of the present invention are non-toxic biodegradable molecules which undergo metabolism in the body to carbon dioxide and water.

The known metabolic pathways for these molecules is first hydrolysis of the glycosidic or ester linkages to yield a long chain alcohol and maltose (in the case of tetradecylmaltoside) or a long chain fatty acid and sucrose (in the case of sucrose monostearate/distearate). The long chain alcohol is oxidized to the corresponding fatty acid which can then be oxidized to $CO_2$ and $H_2O$. The carbohydrate components of the gelators are also hydrolyzed to yield the constituent monosaccharides, glucose in the case of maltose, and glucose and fructose in the case of sucrose. These can then be metabolized by glycolysis and oxidative phosphorylation to $CO_2$ and $H_2O$.

The present invention provides hydrogels which are useful for encapsulating drugs without chemical modification. Furthermore, whereas pi-pi stacking of the phenyl ring in amygdalin hydrogelators is essential to their activity, the gelators of the present invention, such as tetradecylmaltoside and sucrose monostearate/distearate, are capable of self-assembly into stable gels with no aromatic rings purely by hydrogen bonding between the sugar moieties and Van der Waals interactions between the hydrophobic hydrocarbon chains. It was previously thought that all three interactions, those between hydrogen-bond forming carbohydrate groups, pi-pi stacking between phenyl rings and Van der Waals interactions between hydrocarbon chains were essential requirements for gelation to occur.

The gelators described herein, are suitable for forming hydrogels with a variety of therapeutic agents regardless of the agents solubility in aqueous or organic solvents. Thus the hydrogels are suitable for formulation and delivery of drugs of differing chemical composition and properties. As shown in the Examples provided herein, hydrogels have been formulated incorporating drugs with various solubility in aqueous solvents, ranging from insoluble to highly soluble in water. Formation of hydrogels with widely differing solubility properties is possible because the agent being incorporated does not have to be soluble in the hydrogel. The self-assembling gelators which form the matrix of the hydrogel are mild nonionic surfactants which are compatible with both hydrophobic and hydrophilic agents and which can be trapped in the cavities of the gel matrix as it is formed in solutions or suspensions containing the agent and the gelator.

Accordingly, in various aspects, the hydrogels of the present invention allow for encapsulation and delivery of a wide variety of therapeutic agent drugs for which poor solubility and/or the requirement for delayed release make their incorporation into a gel matrix desirable or necessary. Additionally, because the hydrogels may be used in various delivery methods, including but not limited to single dosage forms, transdermal delivery, and nasal or pulmonary delivery, a wide variety of therapeutic agents is intended for use with the hydrogels of the present invention.

Therapeutic peptides (naturally or synthetically derived) and peptide hormones, whether naturally or synthetically derived for use with the invention may be any medically or diagnostically useful peptide or peptide hormone. The peptides or peptide hormones may be of various sizes including up to about 15 kD, 30 kD, 40 kD, 50 kD, 60 kD, 70 kD, 80 kD, 90 kD, 100 kD and larger. Examples of peptides and peptide hormones include vasopressin, vasopressin polypeptide analogs, desmopressin, glucagon, corticotropin (ACTH), gonadotropin, calcitonin, C-peptide of insulin, parathyroid hormone (PTH), growth hormone (HG), human growth hormone (hGH), growth hormone releasing hormone (GHRH), oxytocin, corticotropin releasing hormone (CRH), somatostatin or somatostatin polypeptide analogs, gonadotropin agonist or gonadotrophin agonist polypeptide analogs, human atrial natriuretic peptide (ANP), human thyroxine releasing hormone (TRH), follicle stimulating hormone (FSH), prolactin, insulin, insulin like growth factor-I (IGF-I) somatomedin-C (SM-C), calcitonin, leptin and the leptin derived short peptide OB-3, melatonin, GLP-1 or Glucagon-like peptide-1, GiP, neuropeptide pituitary adenylate cyclase, GM-1 ganglioside, nerve growth factor (NGF), nafarelin, D-tryp6)-LHRH, FGF, VEGF antagonists, leuprolide, interferon (e.g., $\alpha$, $\beta$, $\gamma$) low molecular weight heparin, PYY, LHRH antagonists, Keratinocyte Growth Factor (KGF), Glial-Derived Neurotrophic Factor (GDNF), ghrelin, and ghrelin antagonists. Additionally, sex hormones which can be used include, without limitations, estradiol, diethylstilbestrol, conjugated estrogens, estrone, norethindrone, medroxyprogesterone, progesterone, norgestrel, testosterone, methyltestosterone, fluoxymesterone, and thymosin $\beta$-4.

Nonsteroidal anti-inflammatory agents (NSAIDs) suitable for use with the hydrogels of the present invention are well known in the art and may include, but are not limited to celecoxib; propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; and combinations of any of the foregoing. Additionally, pharmaceutically acceptable analogs of NSAIDs are suitable as well, including salts, esters, amides, prodrugs or other derivatives.

Steroidal anti-inflammatory agents suitable for use with the hydrogels of the present invention are well known in the art and may include, but are not limited to: corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and combinations thereof.

Suitable antibiotic agents for use with the hydrogels of the present invention are well known in the art and may include, but are not limited to: chloramphenicol; synthetic and semi-synthetic penicillins; beta-lactames; quinolones; fluoroquinolones; macrolide antibiotics; peptide antibiotics; cyclosporines; erythromycin; clinndamycin; antibiotics of the lincomycin family; antibiotics of the tetracycline family; and sulfur-based antibiotics, such as sulfonamides. Exemplary antibiotics of the lincomycin family include lincomycin (6,8-dideoxy-6-[[(1-methyl-4-propyl-2-pyrrolidinyl)-carbonyl]amino]-1-thio-L-threo-$\alpha$-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]am-ino]-1-thio-L-threo-$\alpha$-D-galacto-octopyranoside), and other known analogs and/or related. Exemplary antibiotics of the tetracycline family include tetracycline (4-(dimethylamino)1,4,4-$\alpha$-,5,5-$\alpha$-,6,11,12.alpha.-octahydro-3,6,12-,12-$\alpha$-pentahydroxy-6-methyl-1,11-dioxo-2naphthacenecarboxamide), chlortetracycline, oxytetracycline, tetracycline, demeclocycline, rolitetracycline, methacycline and doxycycline and their pharmaceutically acceptable salts and esters. Exemplary sulfur-based antibiotics include, but are not limited to, the sulfonamides sulfacetamide, sulfabenzamide, sulfadiazine, sulfadoxine, sulfamerazine, sulfanethazine, sulfamethizole, sulfamethoxazole, and pharmacologically acceptable salts and esters thereof, such as sulfacetamide sodium.

Anti-viral agents for use with the hydrogels of the present invention are intended to include any agents that inhibit viral replication, such as but not limited to: non-nucleoside reverse transcriptase inhibitors such as Nevirapine, Delavirdine, and Efavirenz; nucleoside reverse transcriptase inhibitors (nucleoside analogs) such as Zidovudine, Didanosine, Zalcitabine, Stavudine, Lamivudine, Abacavir, and Emtricitabine; protease inhibitors such as Amprenavir, Fosamprenavir, Indinavir, lopinavir, Ritonavir, Saquinavir, and Nelfinavir; and nucleotide analog reverse transcriptase inhibitors (NtARTIs or NtRTIs) such as Tenofovir and Adefovir.

Ultra-violet (UV) blocking agents or sunscreen agents may also be incorporated into the hydrogels of the present invention for delivery of the agents to a specific tissue. A variety of UV blocking agents are well known in the art and may include, but are not limited to: UVB blocking agents such as salicylic acid derivatives, cinnamic acid derivatives, liquid $\beta,\beta'$-diphenylacrylate derivatives, p-aminobenzoic acid derivatives, 4-methylbenzylidene camphor, 2-phenylbenzimidazole-5-sulfonic acid, and 1,3,5-triazine derivatives; UVA blocking agents such as dibenzoylmethane derivatives, benzophenone derivatives, silane derivatives or polyorganosiloxanes containing a benzophenone group, anthranilates, silicon derivatives of N-substituted benzimidazolylbenzazoles or of benzofurylbenzazoles, and triazine derivatives; and combinations thereof.

Anti-wrinkle agents for use with the hydrogels of the present invention are intended to include any agents that confer anti-skin atrophy activities, such as but not limited to retinol and retinoic acid derivatives, such as 13-trans retinoic acid, 13-cis retinoic acid and retinyl ester; hydroxy acids, such as hydroxy acid, alpha hydroxy acid, beta hydroxy acid, poly hydroxy acid, glycolic acid, and lactic acid; exfoliants; Coenzyme Q10 copper peptides; kinetins; tea extracts; and collagens.

Anti-malarial agents for use with the hydrogels of the present invention are intended to include, but not limited to quinine; quinimax; quinidine; chloroquine and derivates such as chloroquine phosphate and hydroxychloroquine; amodiaquine; pyrimethamine; sulphadoxine; proguanil; mefloquine; atovaquone; primaquine; artemesinin; halofantrine; doxycycline; and clindamycin. Further, a derivatives of such agents are well known in the art and may be using the present invention.

In various aspects, the hydrogel formulations of the present invention may include one or more preservatives to prevent decomposition by microbial growth or undesirable chemical changes. Various preservatives are well known in the art for use with drug compositions. Examples of preservatives that may be used in the hydrogels of the present invention, include, but are not limited to preservatives such as ethylene diamine tetraacetic acid (EDTA), sodium azide, p-hydroxybenzoate and its analogs, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, chlorobutanol, m-cresol and alkyglycosides such as dodecyl maltoside.

In various aspects, the hydrogel formulations of the present invention are suitable for use in a variety of drug delivery systems. For example, the hydrogel may be formulated for use in single dosage forms suitable for nasal, buccal and/or enteric delivery of the therapeutic agent, such as time release capsules, pills, or sprays. Similarly, the hydrogel may be formulated for use in other delivery methods including transdermal delivery systems, such as transdermal patches, suppositories and the like. Additionally, the hydrogel may be formulated for delivery of a therapeutic agent via the nasal or pulmonary mucosa. As such, the hydrogel formulations described herein may be further admixed with any pharmaceutically acceptable carriers, excipients, flavorants, dyes, and the like depending on the intended delivery system.

The hydrogels of the present invention may be included in single dosage forms that include one or more hydrogel formulations including one or more therapeutic agents. When a single dosage form includes more than one specific hydrogel formulation, the different hydrogels may be in any configuration (i.e., via planar layering or radial layering) and the hydrogels may be separated by a coating or other suitable barrier, such as a membrane, however, physical separation of the layers is not required depending on the gelators used. For example, the entire dosage form or one or more layers therein, may include a suitable enteric coating.

In one aspect, the invention provides a controlled release bilayer formulation. The formulation may include one or more hydrogels and/or coatings with varying dissolution characteristics such that one or more drugs may be released at various times. For example, layered formulations including one or more layers and one or more therapeutic agents may be prepared in which the release of the agents are dependent on the dissolution of the hydrogel by changes in temperature, for example, raising the temperature from 25 degrees C. to 37 degrees C. and/or biodegradation in biological systems due to the activity of enzymes involved in the digestion of food (e.g. enzymes such as glycosidases, including for example, amyloglucosidase and invertase which are involved in the hydrolysis of starch and sucrose respectively and hydrolases of fatty acids, including for example, lipases.

The layered formulations may include any number of different layers and therapeutic agents as necessary for a particular application. Accordingly in one aspect, the formulation may include a first layer and a second layer, wherein the first layer includes a first therapeutic agent entrapped in a first biodegradable hydrogel, and the second layer comprises a second therapeutic agent entrapped in a second biodegradable hydrogel.

In an exemplary aspect, the layered formulation includes encapsulating an inhibitor of dihydrofolate reductase (also known as antifolates), such as methotrexate in a hydrogel composed of an alkylglycoside, and encapsulating a folate, such as folic acid in a hydrogel composed of a sucrose ester. A hydrogel layer of alkyglycoside composed of tetradecylmaltoside is stable at 25 degrees C., however is solubilized at 37 degrees C. In comparison, a hydrogel layer of a sucrose ester, composed of sucrose monostearate/distearate is stable at 37 degrees C., and as a sucrose ester of a fatty acid, it is susceptible to degradation by invertase and lipases in the gastrointestinal tract.

Upon ingesting a hydrogel formulation including folic acid and methotrexate, the methotrexate is expected to be released immediately from the temperature sensitive hydrogel, while the release of the folic acid would require the degradation of the temperature-stable hydrogel by enzymatic activity in the gastrointestinal tract which would delay its release and absorption. Accordingly, in an exemplary aspect, the invention provides a stable, self-assembling, biocompatible and biodegradable multilayer hydrogel formulation including folate and methotrexate allowing for delayed release or controlled release of the incorporated compounds as the hydrogel is degraded in the body. For example, the layered formulation is such that folate is incorporated into a hydrogel which allows folate to be absorbed subsequent to the absorption of the antifolate.

As discussed above, the controlled release hydrogel formulations of the present invention may include one or more suitable enteric coatings. Enteric coatings are well known in the art and may attribute additional time dependent release of the therapeutic agents from the hydrogel formulations.

For example, suitable enteric coatings may be composed of polymers including but not limited to cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Additional examples of suitable enteric polymers include but are not limited to cellulose acetate phthalate, hydroxypropylmethylcellulose phthalate, polyvinylacetate phthalate, methacrylic acid copolymer, shellac, cellulose acetate trimellitate, hydroxypropylmethylcellulose acetate succinate, hydroxypropylmethylcellulose phthalate, cellulose acetate phthalate, cellulose acetate succinate, cellulose acetate malate, cellulose benzoate phthalate, cellulose propionate phthalate, methylcellulose phthalate, carboxymethylethylcellulose, ethylhydroxyethylcellulose phthalate, shellac, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer, methacrylic acid-ethyl acrylate copolymer, methyl acrylate-methacrylic acid-octyl acrylate copolymer, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer, polyvinyl alcohol phthalate, polyvinyl acetal phthalate, polyvinyl butylate phthalate and polyvinyl acetoacetal phthalate, or combinations thereof.

In one aspect, the invention provides a stable, self-assembling, biocompatible and biodegradable hydrogel formulation including one or more of folate, methotrexate, or curcumin allowing for delayed release or controlled release of the incorporated compounds as the hydrogel is degraded in the body. Methotrexate is a folate antagonist which has been used for the treatment of various malignancies since the 1960's and which has also been used in lower dosage in the treatment of autoimmune diseases such as psoriasis and rheumatoid arthritis. Because methotrexate interferes with folic acid metabolism when given in high dosage as an antineoplastic agent, folinic acid, a metabolite of folic acid is often given as a "rescue" agent to rescue normal cells from the toxic effects of methotrexate. However, the much lower doses used as suppressors of autoimmune diseases are such that, with administration of folic acid, most of the toxic effects can be avoided. Under these circumstances, the methotrexate can be given in conjunction with folic acid and its analogues.

In the past it has been necessary to give the folic acid and methotrexate in separate compositions. The folic acid and the methotrexate are given on different days. For example, the folic acid may be administered daily 3-5 times a week and the methotrexate administered on a day when the folic acid is not given. This method of dosing presents problems, since it is essential that the patient remember dosage and schedule when each active agent is to be taken. It is not advisable to have the patient absorb both the folic acid (a vitamin) and the methotrexate (an antivitamin) simultaneously. It is beneficial if folic acid and/or one or more of its analogues, including salts thereof, could be administered in the same formulation as the inhibitor of dihydrofolate reductase. Accordingly, in one aspect, the present invention provides formulations containing inhibitors of dihydrofolate reductase (antifolates) and folic acid, its salts or analogues, including protected forms of folic acid, wherein the folate is in a form that will be absorbed subsequent to the absorption of the antifolate. Additional inhibitors of dihydrofolate reductase suitable for use, include 10-deazaminopterin, aminopterin and trimethoprim.

In terms of the combined use of folic acid and methotrexate for the treatment of rheumatoid arthritis, there is currently no adequate method for administering the two drugs together to achieve controlled release of the folic acid without altering the pharmacokinetic profile of methotrexate. It is not advisable to have the patient absorb both the folic acid (a vitamin) and the methotrexate (an antivitamin) simultaneously The distinct properties of the gelators described herein allow for preparation of a bilayer hydrogel formulation in which the immediate release of methotrexate from the alkylglycoside hydrogel layer can occur due to the thermolability of the gel at 37 degrees C. while the delayed controlled release of folic acid is possible by entrapping it in a hydrogel layer of sucrose monostearate/sucrose distearate which is stable at 37 degrees C. but which is biodegradable due to the action of enzymes in the gastrointestinal tract thereby providing simultaneous administration of folate and methotrexate.

Accordingly, in one aspect, the invention provides a method of treating rheumatoid arthritis. The method includes administering to a subject in need thereof a therapeutically effective amount of a controlled release bilayer formulation. The formulation may include a first layer and a second layer, such that the first layer includes methotrexate and the second layer includes folic acid. In an exemplary aspect, the first layer includes methotrexate entrapped in a tetradecylmaltoside biodegradable hydrogel, and the second layer includes folic acid entrapped in a sucrose stearate biodegradable hydrogel.

Combination therapy with folate and methotrexate is expected to provide an easier and more effective means to administer therapy with the drugs in patients who are generally on complicated drug regimens. Methotrexate is the most widely prescribed disease-modifying antirheumatic drug for these patients and no other compounds or biological products have the efficacy profile of methotrexate. Therefore, simplifying its administration while at the same time reducing its toxicity is expected to have tremendous impact on clinical practice.

As discussed herein, the hydrogel formulations of the present invention are suitable for use in transdermal delivery systems, such as transdermal patches, wherein the hydrogel formulation including one or more therapeutic agents is contained within a laminated structure, that serves as a drug delivery device, which may be affixed to the skin.

The hydrogel formulations of the present invention are intended for use in any suitable transdermal delivery system. In one embodiment, the hydrogel formulation may be contained in a layer, or "reservoir", underlying an upper backing layer. The laminated structure may contain a single reservoir, or it may contain multiple reservoirs, each layer including a different agent and/or a hydrogel formulated with a different gelator.

In one embodiment, the reservoir comprises a polymeric matrix of a pharmaceutically acceptable contact adhesive material that serves to affix the system to the skin to allow transdermal application of the therapeutic agent. Suitable skin contact adhesive materials are well known in the art and include, but are not limited to: polyethylenes; polysiloxanes; polyisobutylenes; polyacrylates; polyurethanes; and the like. The particular polymeric adhesive selected will depend on the particular therapeutic agent and hydrogels used. For example the adhesive should be compatible with all components of the hydrogel formulations. The reservoir and skin contact adhesive may be configured as separate and distinct layers, with the adhesive underlying the reservoir which may include one or more hydrogel layers including one or more therapeutic agents.

The backing layer of the transdermal device, which serves as the upper surface of the device, functions as the primary structural element of the laminated structure and may provide the device with flexibility. The material may be impermeable to the hydrogel formulations and to any other components of the layered device to prevent loss of any components through the upper surface of the device. The backing layer may be made of a sheet or film of a flexible elastomeric material, such as, but not limited to, polyethylene, polypropylene, and polyesters. Additionally, the device may include a release liner which may be removed prior to use to expose the dermal contact surface so that the system may be affixed to the skin.

Accordingly, in one aspect, the invention provides a method for transdermal delivery of a therapeutic agent to a subject in need thereof using transdermal delivery device described herein.

The hydrogels prepared for use in transdermal application may include a hydrogel formed using an alkylglycoside or sucrose ester, a therapeutic agent, and an acetate buffer. In an exemplary aspect, the hydrogel is formed from sucrose stearate, sucrose distearate or a combination thereof. As described above, the hydrogel may further include a preservative.

In an exemplary embodiment, the preservative is ethylene diamine tetraacetic acid (EDTA), benzalkonium chloride, sodium azide or dodecyl maltoside. Additionally, the acetate buffered hydrogel may have a pH of about 4 to 8, 4.5 to 7.5, 4.5 to 6.5, or 5 to 6. As discussed further in the Examples, acetate buffered hydrogels are stable for a least 120 days at 37 degrees C.

While any suitable therapeutic agent is contemplated for use in transdermal applications, exemplary agents include peptides, hormones, steroids, anti-inflammatories, anti-biotics, anti-virals, UV blockers, and anti-wrinkle agents. For example, in one embodiment, the therapeutic agent is a steroid, such as testosterone. In another embodiment, the therapeutic agent is an anti-wrinkle agent, such as, but not limited to retinol and retinoic acid derivatives, such as 13-trans retinoic acid, 13-cis retinoic acid and retinyl ester; hydroxy acids, such as alpha hydroxy acid, beta hydroxy acid, poly hydroxy acid, glycolic acid, and lactic acid; exfoliants; Coenzyme Q10 copper peptides; kinetins; tea extracts; and collagens.

In various aspects of the invention, the hydrogel formulations described herein may include dextromethorphan (DXM or DM). Dextromethorphan is an antitussive (cough suppressant) as well as being found effective for treatment of various ailments from pain relief to psychological applications. Exemplary hydrogel formulations including dextromethorphan may be prepared for any of the delivery routes described herein.

In an exemplary aspect, the present invention provides a transdermal device including a hydrogel incorporating thymosin β-4 as the therapeutic agent. β-thymosins are the primary regulators of unpolymerized actin, and are essential for maintaining the small cytoplasmic pool of free G-actin monomers required for rapid filament elongation and allowing for the flux of monomers between the thymosin-bound pool and F-actin. Thymosin β-4 sequesters actin, holding it in a form that is unable to polymerize. Due to its profusion in the cytosol and its ability to bind ATP G-actin but not F-actin, thymosin β-4 is regarded as the principal actin-sequestering protein. Thymosin β-4 binds ATP G-monomeric actin in a 1:1 complex where G-actin cannot polymerize. Increase in cytosolic concentrations of thymosin β-4 increases the concentration of sequestered actin subunits and correspondingly decreases F-actin due to actin filaments being in equilibrium with actin monomers. Thymosin β-4 has been shown to accelerate epidermal wound healing. For example, when applied topically or administered via injection in vivo in wound healing models, thymosin β-4 has been shown to accelerate epithelial layer healing. Furthermore, thymosin β-4, has been shown to stimulate collagen deposition in the wound and angiogenesis, as well as stimulating keratinocyte migration, resulting in the wound contracting to close the skin gap in the wound.

As discussed herein, the hydrogel formulations of the present invention are suitable for delivery of therapeutic agents via the intranasal and/or pulmonary mucosa. Exemplary hydrogel formulations for use in nasal or pulmonary delivery applications include acetate buffered hydrogels as described herein, including a therapeutic agent, an alkylglycoside or sucrose ester, and an acetate buffer. The hydrogels allow increased residency time upon the intranasal or pulmonary mucosa providing improved absorption of the therapeutic agent.

Accordingly, in one aspect, the invention provides a method for increasing the residency time of a therapeutic agent during intranasal or pulmonary delivery of the agent to a subject. The method includes applying to the nasal or pulmonary mucosa of the subject a composition including an alkylglycoside or sucrose ester, an acetate buffer, and a therapeutic agent, thereby increasing the residency time of the therapeutic agent in the nasal or pulmonary mucosa. In an exemplary embodiment, the hydrogel includes a sucrose ester, such as sucrose stearate.

It has been reported that orally administered methylene blue (methylthioninium chloride) is effective as a monotherapy in treating people with Alzheimer's disease when administered at a dose of 60 mg. It was found that, at 24 weeks, methylene blue produced a significant improvement relative to placebo in the standard Alzheimer's Disease Assessment Scale-Cognitive Subscale (ADAS-cog) showing an 81 percent reduction of progression of decline over 50 weeks. For subjects remaining on treatment for 84 weeks, there was no statistically significant decline from the baseline values determined at the beginning of the study. It has been demonstrated that intranasal administration of drugs provides increased absorption into the central nervous system and brain through uptake into the olfactory bulb. The olfactory bulb is essentially an extension of the brain into the nasal cavity and allows circumvention of the blood brain barrier and drug absorption.

Unfortunately, aqueous solutions of methylene blue are highly colored and when administered using currently known nasal spray formulations, they often drip out of the naris leaving a visible blue stain on the exterior of the nose or upper lip. Accordingly, in an exemplary embodiment, the present invention provides an aqueous hydrogel as described herein, containing methylene blue, at least one alkylsaccharide, such as an alkyglycoside or sucrose ester, and an aqueous buffer is prepared which may be used for intranasal administration to treat patients with Alzheimer's Disease. Intranasal administration of the hydrogel formulation prevents the methylene blue from exiting the naris and increases residence time of the drug in the nasal cavity, further improving absorption of the drug into the CNS, as well as into systemic circulation. Residual drug and hydrogel components are removed from the nose to the normal mucocilliary clearance process in which material is brought into the back of the throat with a typical halftime of clearance of approximately 15 to 20 minutes thus avoiding leakage of methylene blue from the naris. Accordingly, the present invention provides a method for treating Alzheimer's Disease comprising administering to the nasal or pulmonary mucosa a subject in need thereof a therapeutically effective amount of a composition comprising methylene blue, an alkylglycoside or sucrose ester or combination thereof, and an aqueous buffer. In exemplary embodiments, hydrogel is applied in which the methylene blue dosage is about 30 mg, 60 mg, or 120 mg.

The following examples are provided to further illustrate the embodiments of the present invention, bur are not intended to limit the scope of the invention. While they are typical of those that might be used, other procedures, methodologies, or techniques known to those skilled in the art may alternatively be used.

Example 1

Preparation of Hydrogels

This example illustrates the preparation of hydrogels that include curcumin, folates and/or methotrexate that exhibit sustained or delayed release of the drug.

Various hydrogels were produced that where stable, self-assembling, biocompatible and biodegradable hydrogels into which folate and/or methotrexate are incorporated allowing for delayed release or controlled release of the incorporated compounds as the hydrogel is degraded in the body. The hydrogels were produced using alkylmaltosides and the sucrose esters of long chain fatty acids alkymaltosides.

Alkylmaltosides, such as tetradecylmaltoside can also self-assemble at room temperature over a period of several days to form a stable fibrous matrix which can encapsulate methotrexate and incorporate it into a hydrogel.

Based on the properties of alkylglycosides to self assemble, several hydrogels were made using alkylmaltosides. FIG. 1 shows hydrogels of folate and methotrexate. Sample M-3 is a hydrogel composed of 2% tetradecylmaltoside and 2.5 mg/ml methotrexate. Sample N-4 is a hydrogel composed of 2% sucrose stearate/distearate and 2.5 mg/ml folic acid. Sample M-1 is a bilayer hydrogel composed of 2% tetradecylmaltoside/2.5 mg/ml methotrexate in the bottom layer and 2% sucrose stearate/distearate/2.5 mg/ml folic acid in the top layer.

Figure 2:
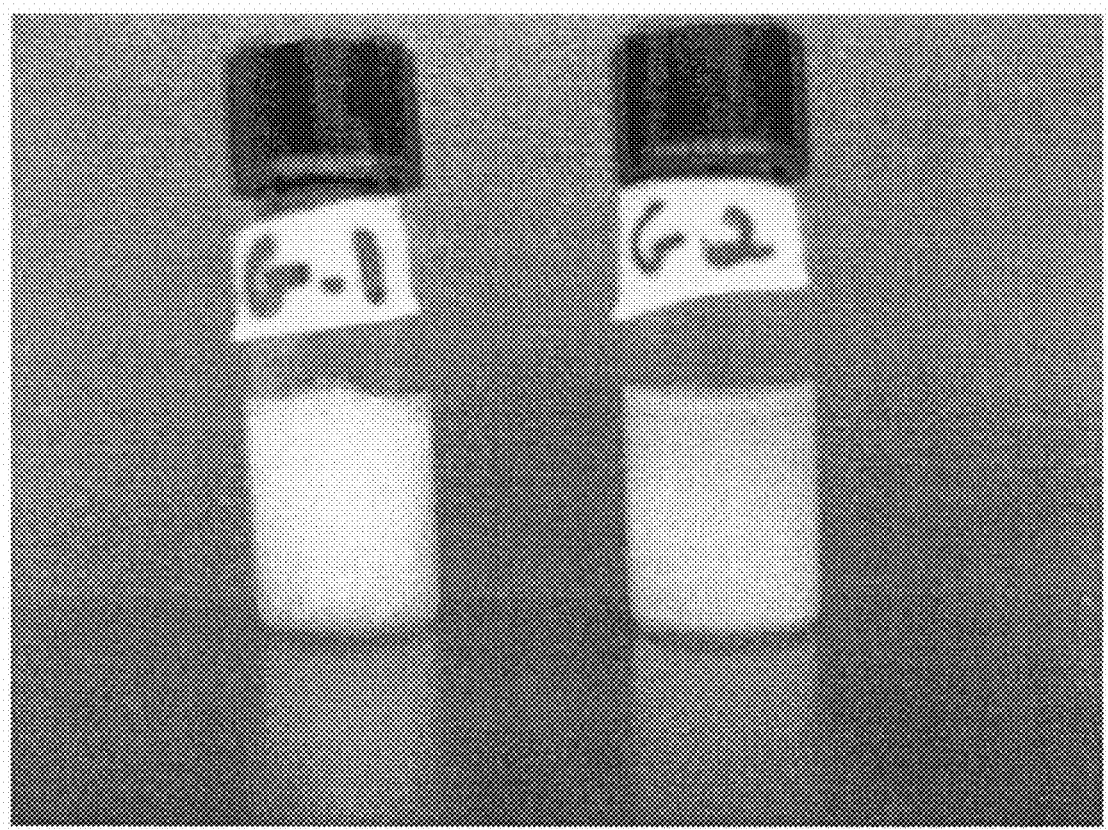
FIG. 2 is a pictorial representation showing hydrogels of folate in tetradecylmaltoside. Sample G-1 is a hydrogel composed of 2% tetradecylmaltoside and 2.5 mg/ml folic acid. Sample G-2 is identical to sample G-1 but has been warmed to 37 degrees C. for 1 hour liquefying the hydrogel and releasing the folic acid.
Figure 3:
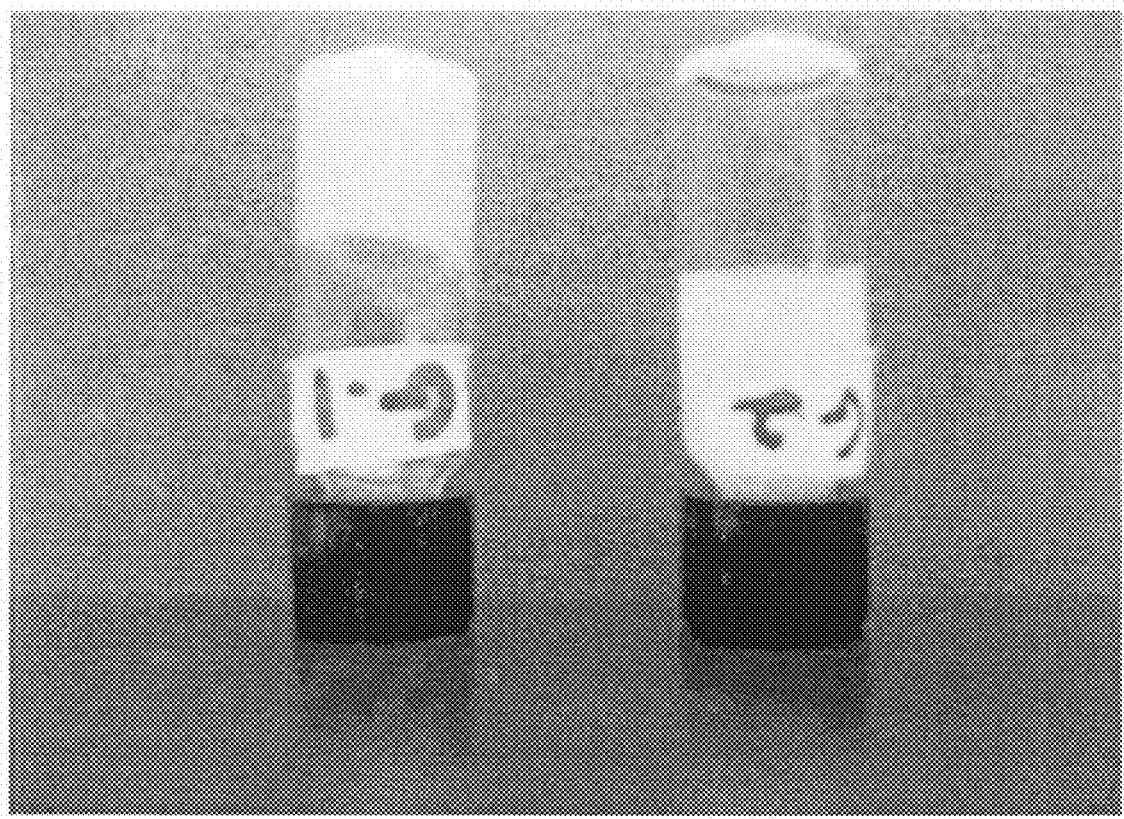
FIG. 3 is a pictorial representation showing the thermostability of hydrogels of folate in tetradecylmaltoside. The hydrogels are those shown in FIG. 2. Sample G-1 is a firm gel which is stable to inversion while sample G-2, identical to the hydrogel of sample G-1 liquefies at 37 degrees C. and is no longer stable to inversion.

FIGS. 2 and 3 show a hydrogel of tetradecylmaltoside with encapsulated folic acid distributed uniformly throughout the gel. The hydrogel spontaneously self-assembles from a solution of 2% tetradecylmaltoside containing 2.5 mg/ml of folic acid at room temperature (25 degrees C.). At 25 degrees C. the hydrogel is stable indefinitely, but when the temperature is raised to 37 degrees C. the gel dissolves leaving a suspension of folic acid in the aqueous solution containing tetradecylmaltoside.

Figure 6:
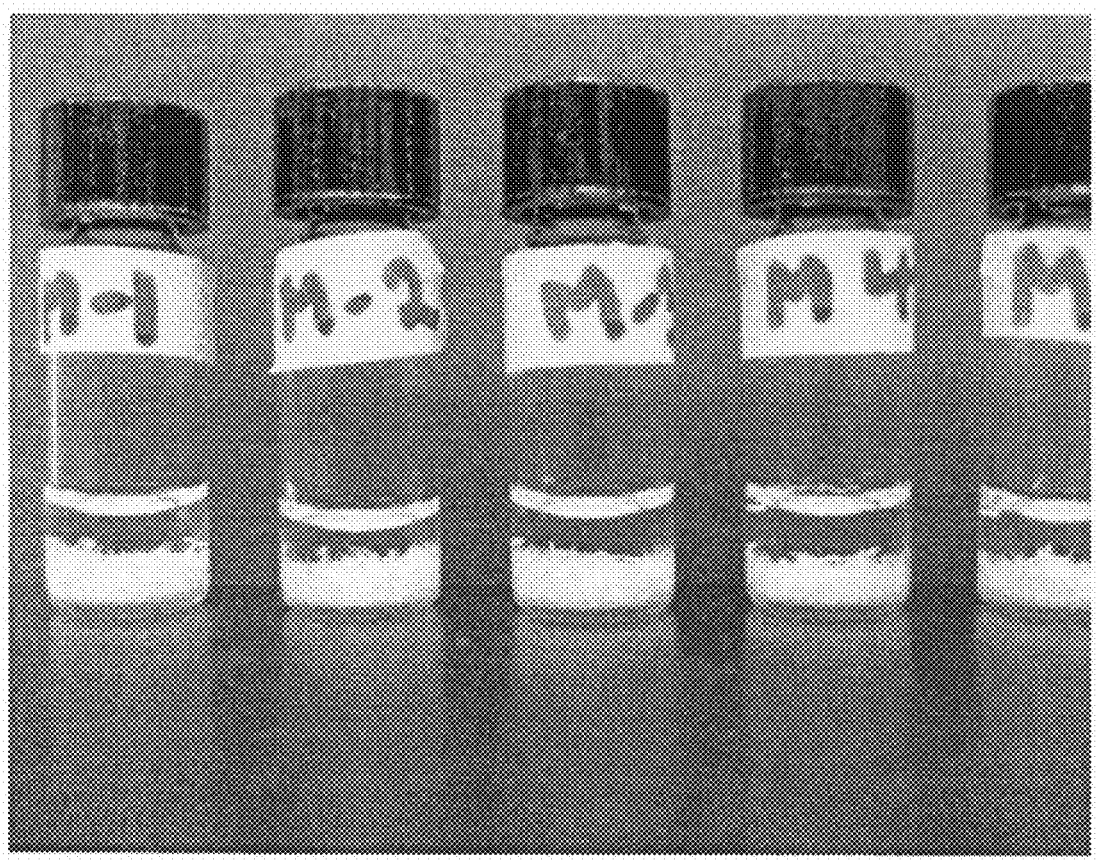
FIG. 6 is a pictorial representation showing the formation of fibrous matrix of tetradecylmaltoside with methotrexate. Samples M-1 to M-5 are identical samples containing 2% tetradecylmaltoside and 2.5 mg/ml methotrexate.
Figure 7:
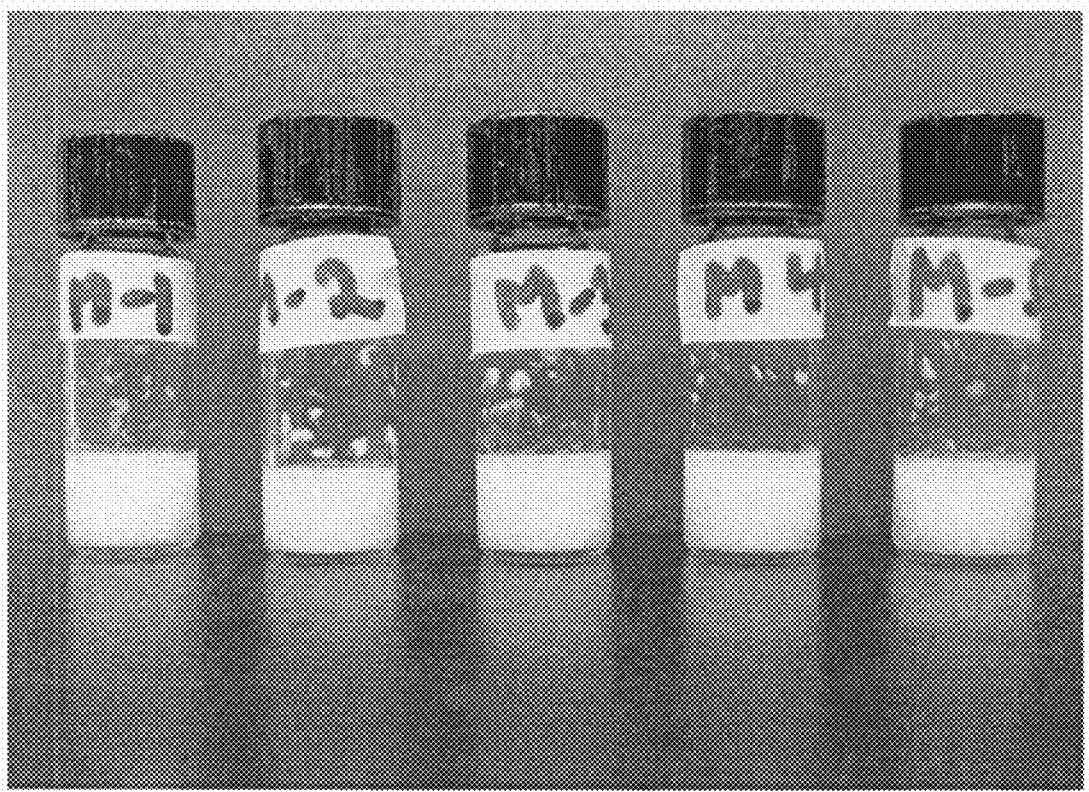
FIG. 7 is a pictorial representation showing the hydrogels of methotrexate in tetradecylmaltoside. The hydrogels are formed from samples shown in FIG. 6. Methotrexate is distributed throughout the fibrous gel matrix.
Figure 8:
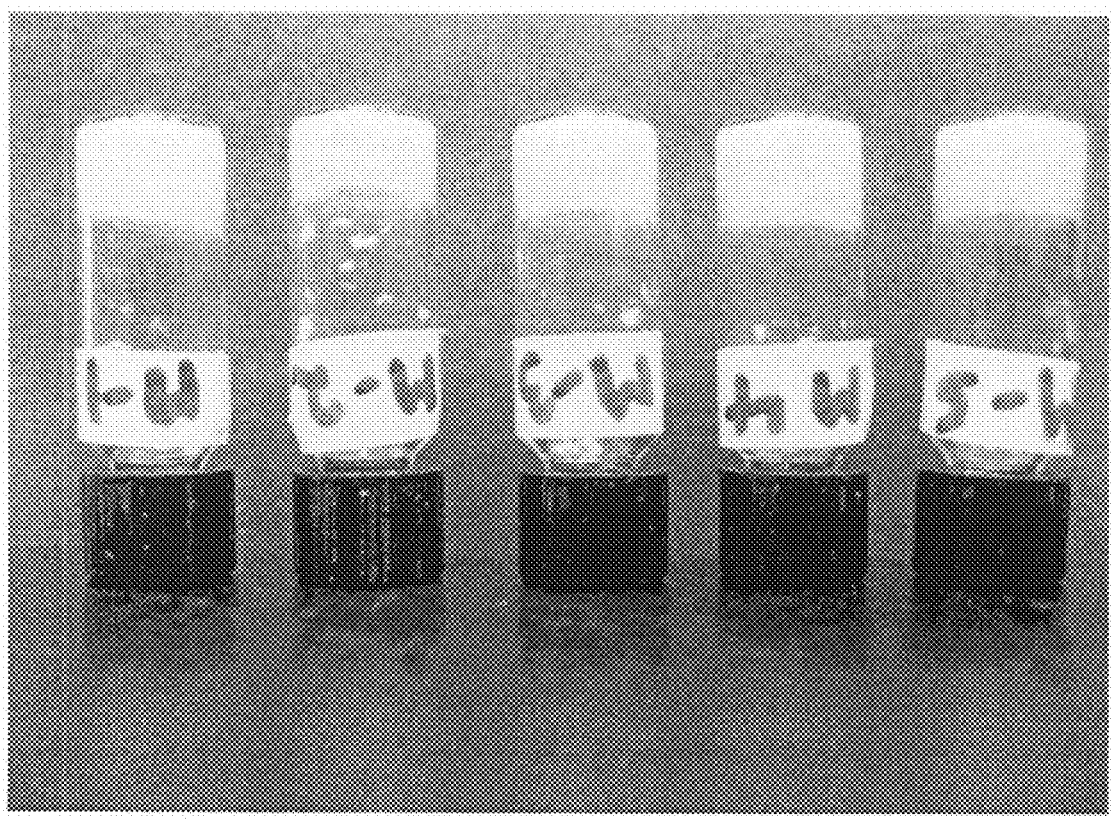
FIG. 8 is a pictorial representation showing the stability of hydrogels of methotrexate in tetradecylmaltoside to inversion. The hydrogels are those shown in FIG. 7.

FIG. 6 shows a stage in the formation of the fibrous matrix of the gel one day after a suspension of 2.5 mg/ml of methotrexate is made in 2% tetradecylmaltoside. The reproducibility of the self-assembly is evidenced by the almost identical appearance of five identical samples. After the samples are vortexed and left to stand at room temperature for 3-4 days the matrix enlarges and completely encapsulates the methotrexate and solution to form identical hydrogels of methotrexate which are stable to inversion (see FIGS. 7 and 8).

Figure 4:
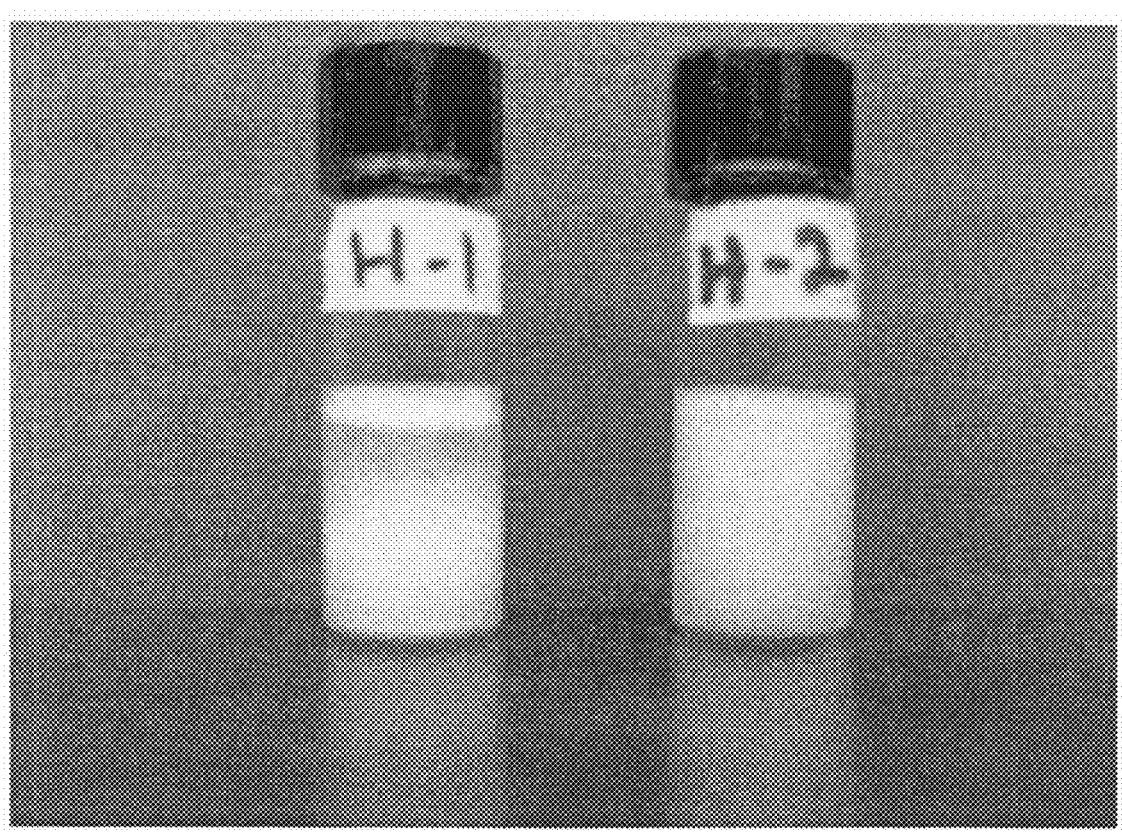
FIG. 4 is a pictorial representation showing hydrogels of folate in sucrose stearate/distearate. Sample H-1 is a suspension of 2.5 mg/ml folic acid in 2% sucrose stearate/distearate which does not gel at 25 degrees C. Sample H-2 is a hydrogel of sucrose stearate/distearate with encapsulated folic acid which forms upon cooling after heating the suspension for 1 hour at 37 degrees C.
Figure 5:
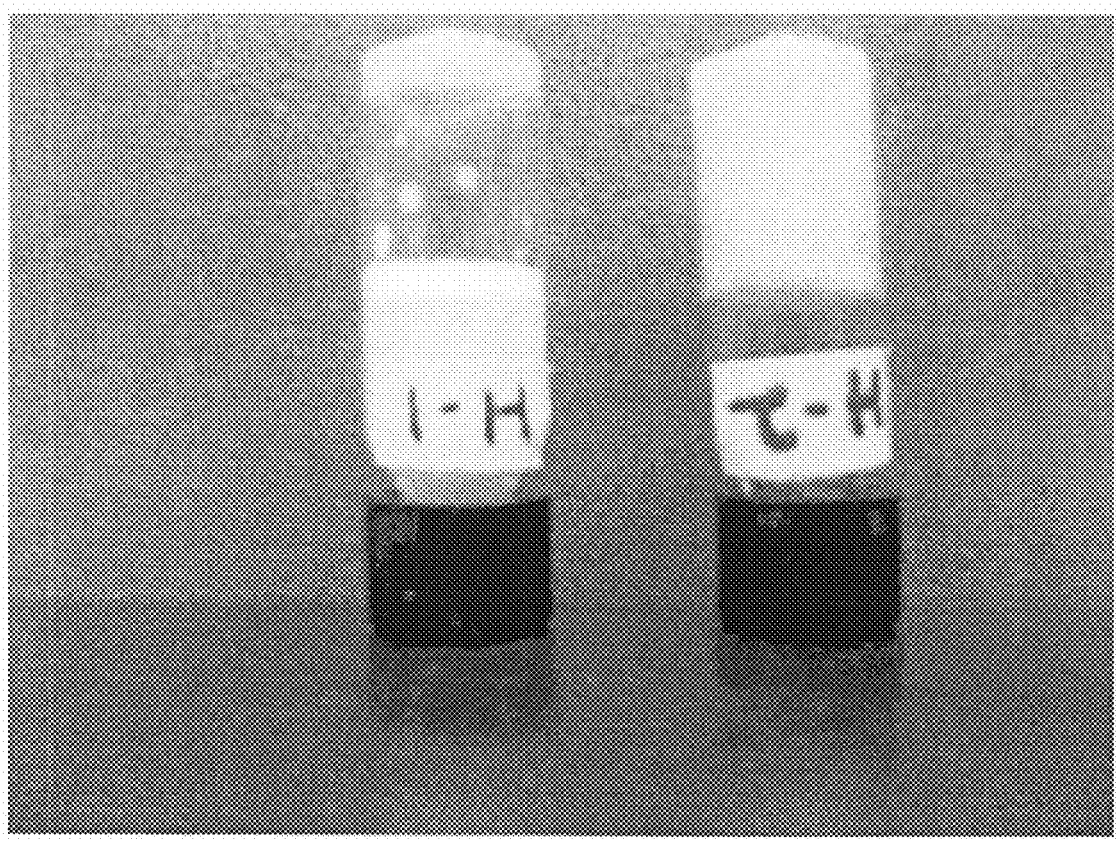
FIG. 5 is a pictorial representation showing the stability of hydrogels of folate in sucrose stearate/distearate. The hydrogels are those shown in FIG. 4. Sample H-1 is a loose suspension which is not stable to inversion while in sample H-2, the suspension of sample H-1 has been converted into a firm hydrogel which is stable to inversion.

Sucrose esters were also used to produce various hydrogels. A mixture of the sucrose esters of the long chain fatty acid stearic acid, sucrose monostearate/sucrose distearate, available commercially from Croda Inc. as Crodesta F-110, is a mild nonionic surfactant which conforms to 21 C.F.R. §172.859 for food use. Sucrose monostearate/distearate (2%) and 2.5 mg/ml folic acid form a loose yellow suspension which does not gel when left at room temperature (25 degrees C.). However, when the suspension is heated to 37 degrees C. for 1 hour, mixed by vortexing, and then left to cool at room temperature the mixture forms a true hydrogel, stable to inversion, in which the folic acid is distributed uniformly throughout the gel. FIGS. 4 and 5 show the appearance of hydrogels of sucrose stearate/distearate with encapsulated folic acid.

Once formed, the sucrose monostearate/distearate hydrogel with encapsulated folic acid is stable indefinitely at room temperature (25 degrees C.) and softens, but does not liquefy at 37 degrees C. When heated to 45 degrees C. for 1 hour and 15 minutes the gel liquefies to a yellow homogeneous suspension which reforms to a gel upon cooling.

Figure 9:
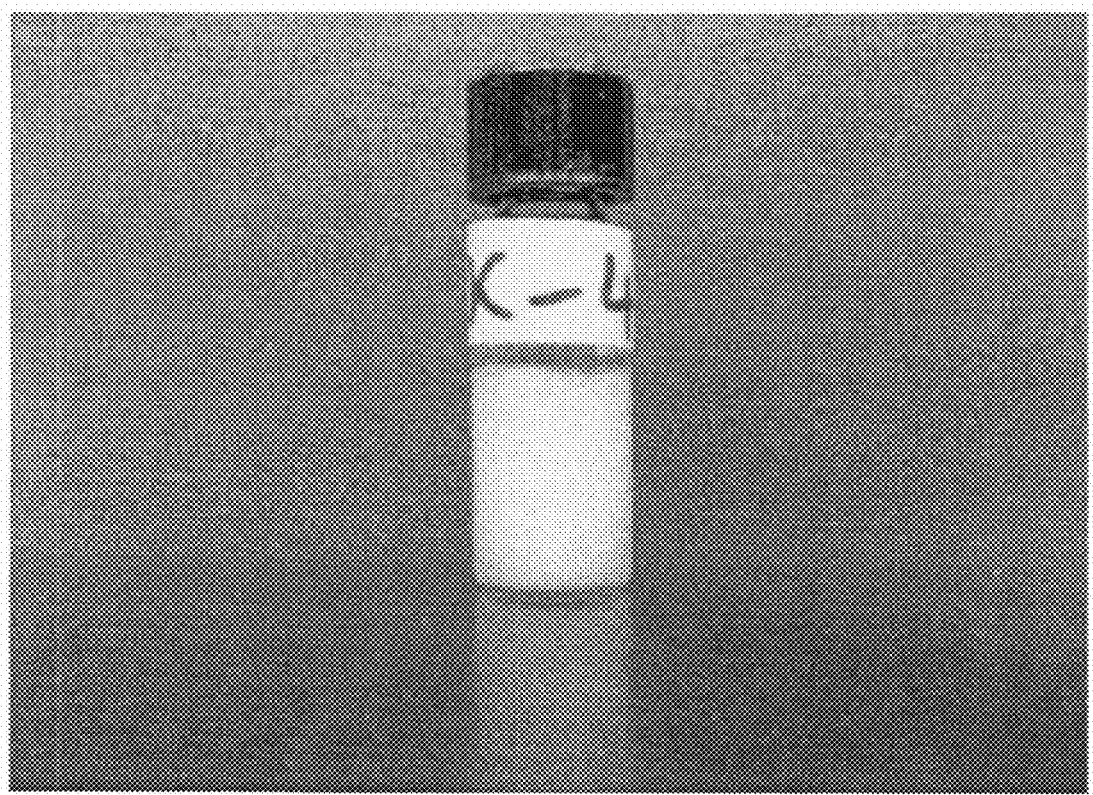
FIG. 9 is a pictorial representation showing a hydrogel of methotrexate in sucrose stearate/distearate. Sample K-4 is a hydrogel composed of 2.5 mg/ml methotrexate in 2% sucrose stearate/distearate.
Figure 10:
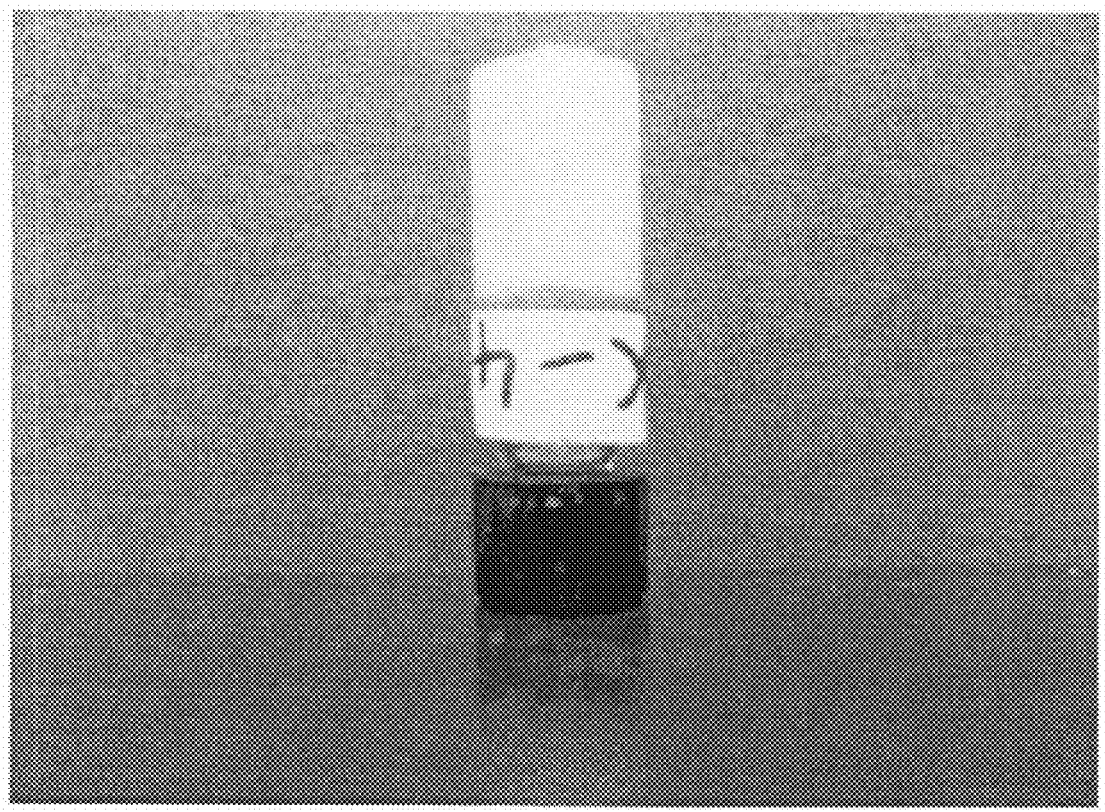
FIG. 10 is a pictorial representation showing the stability of the hydrogel shown in FIG. 9 to inversion.

Additional stable hydrogels in which methotrexate is encapsulated in a gel formed of sucrose stearate/distearate were also prepared. When 2.5 mg/ml of methotrexate was suspended in 2% sucrose monostearate/distearate and left to stand at room temperature the mixture did not gel. However, after heating to 37 degrees C. for 1 hour, mixing by vortexing and cooling at room temperature a stable hydrogel was formed in which methotrexate was distributed uniformly throughout the gel (FIGS. 9 and 10).

Figure 11:
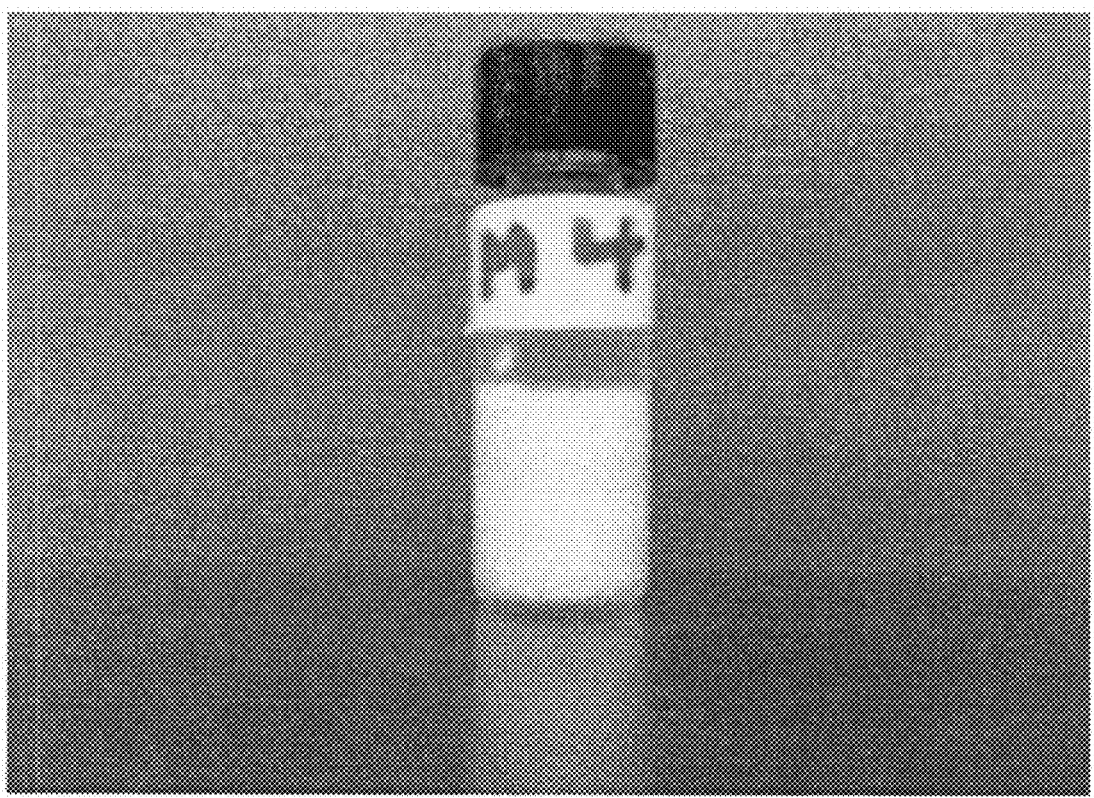
FIG. 11 is a pictorial representation showing a bilayer hydrogel of folate and methotrexate in which the folate is layered on top of the methotrexate. Sample M-4 is a hydrogel composed of 2% tetradecylmaltoside/2.5 mg/ml methotrexate in the bottom layer and 2% sucrose stearate/distearate/2.5 mg/ml folic acid in the top layer. Note the sharp demarcation between the two layers indicated by the different shade of yellow color of the two compounds.

Bilayer hydrogels containing both folic acid and methotrexate were also prepared. FIG. 1 and FIG. 11 shows such a hydrogel in which 2% tetradecylmaltoside/2.5 mg/ml methotrexate comprises the bottom layer of the gel and 2% sucrose stearate/distearate containing 2.5 mg/ml folic acid comprises the top layer. A composite gel of this type containing two different compounds in two hydrogelators of different properties would allow differential release of the compounds encapsulated in the gel by exploiting the differences in thermolability and enzyme sensitivity of the hydrogelators. For example the bilayer hydrogel shown in FIG. 1 would release the encapsulated methotrexate rapidly due to the liquefication of the tetradecylmaltoside layer at the body temperature of 37 degrees C., while a delayed release of the folic acid from the sucrose stearate/distearate layer would occur, since this layer is thermostable at 37 degrees C., but would be susceptible to enzymatic degradation of the gelator by esterases and lipases present in the gastrointestinal tract. This bilayer gel was created by first forming the tetradecylmaltoside/methotrexate hydrogel at 25 degrees C. and then layering a suspension of folic acid in sucrose stearate/distearate, which had been heated to 37 degrees and allowed to cool, on top of the gelled tetradecylmaltoside layer and allowing it to gel.

Figure 12:
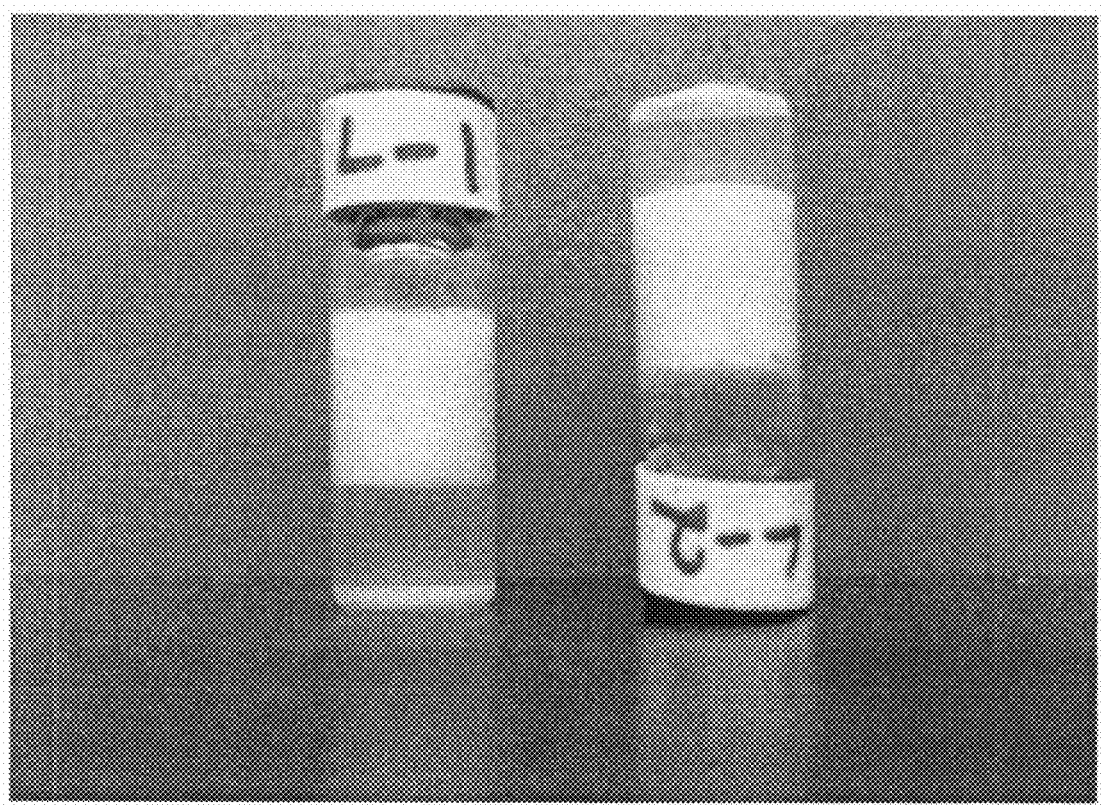
FIG. 12 is a pictorial representation showing bilayer hydrogels of folate and methotrexate in which the methotrexate is layered on top of the folate. Sample L-1 is a hydrogel composed of 2% tetradecylmaltoside/2.5 mg/ml methotrexate in the bottom layer and 2% sucrose stearate/distearate/2.5 mg/ml folic acid in the top layer. Sample L-2 is identical to sample L-1 and demonstrates that the bilayer is stable to inversion.

Interestingly, if a suspension of 2.5 mg/ml of methotrexate in 2% tetradecylmaltoside is layered on top of a hydrogel consisting of 2.5 mg/ml of folic acid in 2% sucrose stearate/distearate the layers invert resulting in a bilayer hydrogel in which the tetradecylmaltoside/methotrexate comprises the bottom layer and the sucrose stearate/distearate/folic acid forms the top layer. The inversion is apparently due to the differences in density between the two gelators. The bilayer hydrogel formed in this manner is stable to inversion and contains a semi-transparent layer of trapped methotrexate on the bottom and a homogeneous hydrogel of folic acid on top (FIG. 12).

Figure 13:
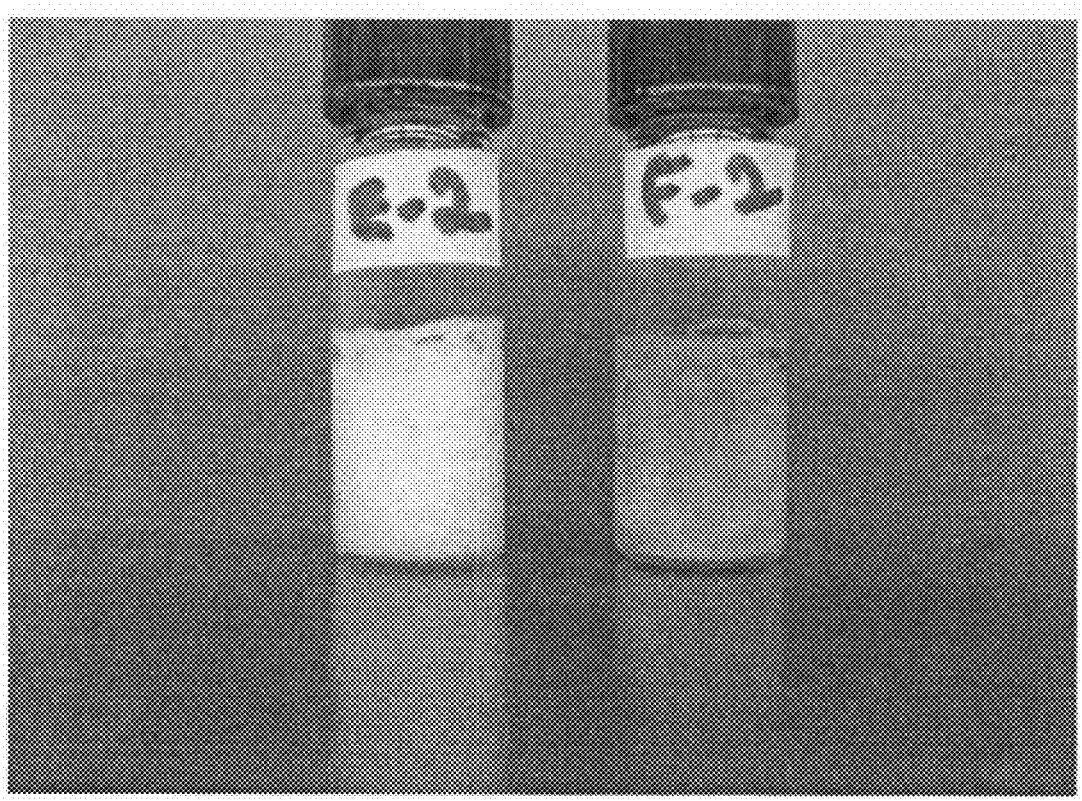
FIG. 13 is a pictorial representation showing hydrogels of curcumin. Sample E-2 is a hydrogel composed of 2% tetradecylmaltoside and 1 mM curcumin. Sample F-2 is a hydrogel composed of 2% tetradecylmaltoside, 1 mM curcumin, and 0.1 M sodium bicarbonate.

Curcumin was also used in the preparation of hydrogels. Curcumin is a natural product isolated from the root of *Curcuma longa* from which the spice turmeric is obtained. It has been reported to have potent antioxidative, anti-inflammatory and antiseptic properties, but has extremely low solubility in water and poor bioavailability which limits its pharmaceutical use. By encapsulating curcumin in a hydrogel composed of 2% tetradecylmaltoside a concentration of the compound in the gel can be obtained which is about 33,000 times higher than the solubility of curcumin in water, for example $1 \times 10^{-3}$ M in the hydrogel vs. $3 \times 10^{-8}$ M in water. The resulting gels are yellow or yellow-orange in color depending on whether sodium bicarbonate is present during the formulation of the gel (see FIG. 13). FIG. 13 is a pictorial representation showing hydrogels of curcumin. Sample E-2 is a hydrogel composed of 2% tetradecylmaltoside and 1 mM curcumin. Sample F-2 is a hydrogel composed of 2% tetradecylmaltoside, 1 mM curcumin, and 0.1 M sodium bicarbonate.

The hydrogels thus formed are comparable to those which have been reported with amygdalin hydrogelators, but unlike amygdalin which is a toxic constituent of apple, almond, peach, cherry and apricot pits that was touted as the controversial anticancer drug laetrile, tetradecylmaltoside is non-toxic and is metabolized to $CO_2$ and $H_2O$ in the body by normal metabolic pathways.

Figure 14:
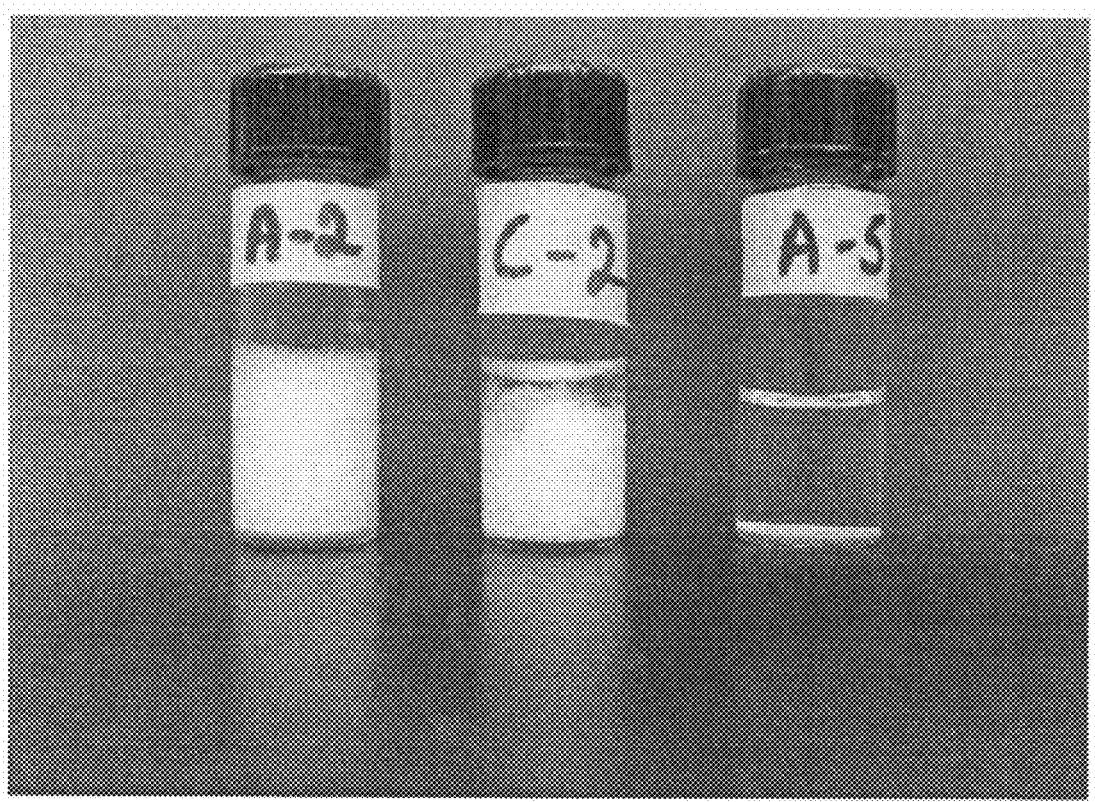
FIG. 14 is a pictorial representation showing hydrogels of 2% tetradecylmaltoside. Sample A-2 is a hydrogel composed of 2% tetradecylmaltoside and 2.5 mg/ml folic acid. Sample C-2 is a hydrogel containing only 2% tetradecylmaltoside. Sample A-5 is a solution of 2.5 mg/ml folic acid in water.
Figure 15:
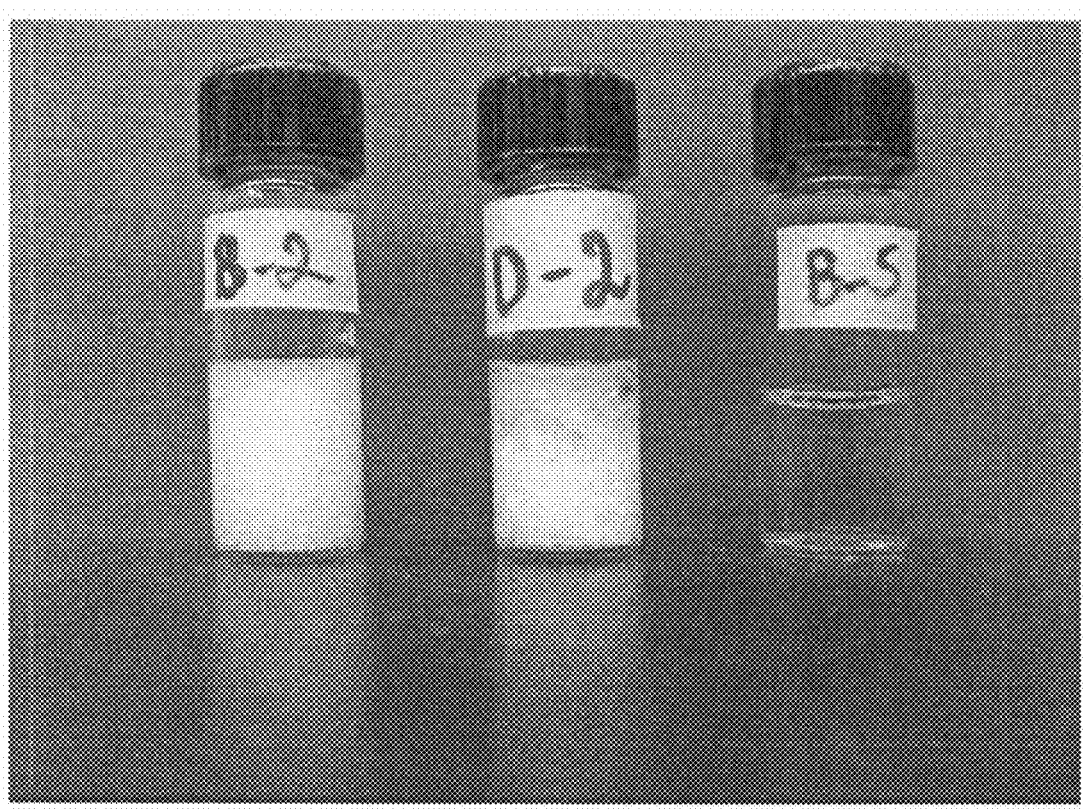
FIG. 15 is a pictorial representation showing hydrogels of 2% tetradecylmaltoside in 0.1 M sodium bicarbonate. Sample B-2 is a hydrogel composed of 2% tetradecylmaltoside and 2.5 mg/ml folic acid in 0.1 M sodium bicarbonate. Sample D-2 is a hydrogel containing only 2% tetradecylmaltoside in 0.1 M sodium bicarbonate. Sample B-5 is a solution of 2.5 mg/ml folic acid in 0.1 M sodium bicarbonate.
Figure 16:
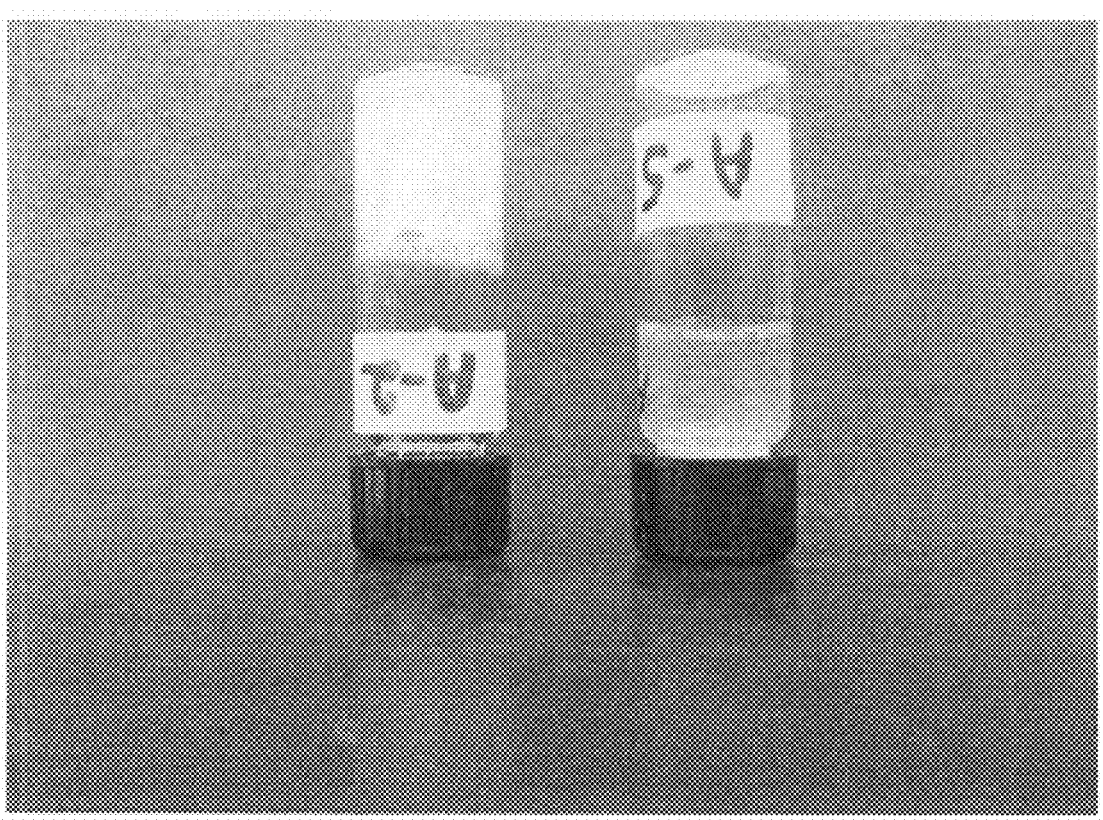
FIG. 16 is a pictorial representation showing the stability of hydrogels of 2% tetradecylmaltoside and 2.5 mg/ml folic acid to inversion. The hydrogels are those shown in FIG. 14. Sample A-2 is a firm gel which is stable to inversion as compared to the solution/suspension of folic acid in water of sample A-5.
Figure 17:
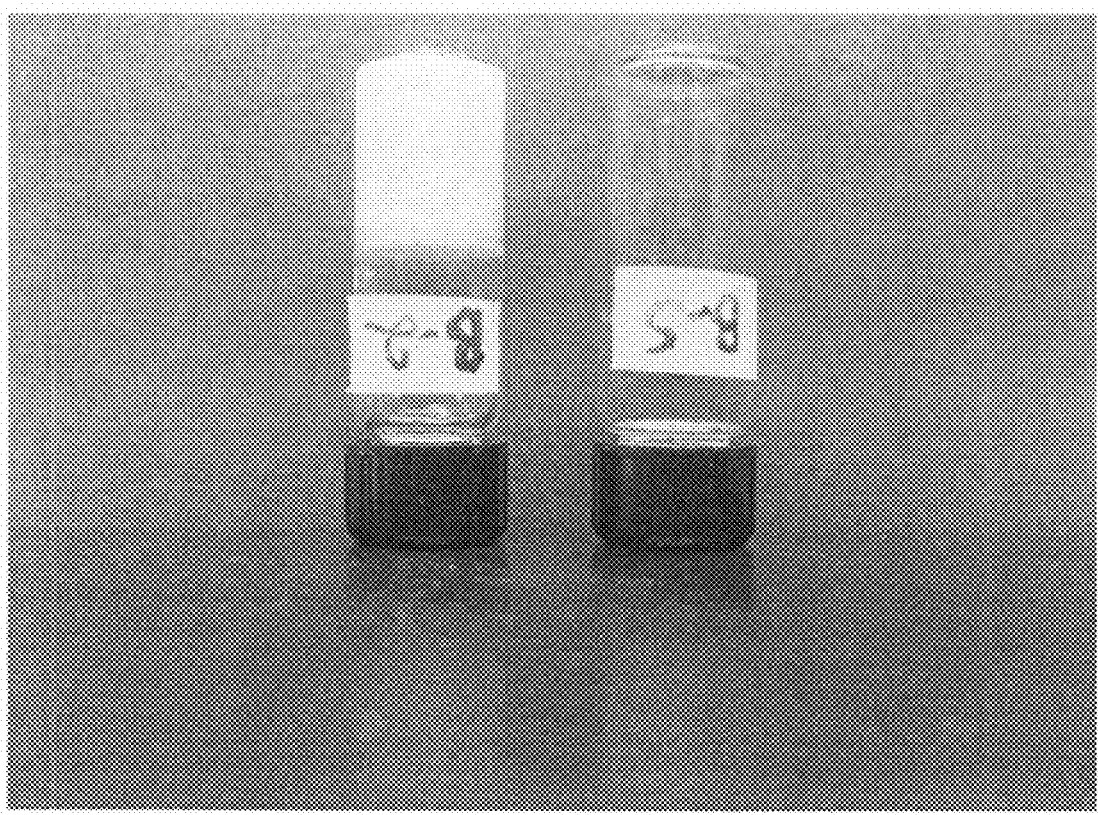
FIG. 17 is a pictorial representation showing the stability of hydrogels of 2% tetradecylmaltoside and 2.5 mg/ml folic acid in 0.1 M sodium bicarbonate to inversion. The hydrogels are those shown in FIG. 15. Sample B-2 is a firm gel which is stable to inversion as compared to the solution of folic acid in 0.1 M sodium bicarbonate in sample B-5.
Figure 18:
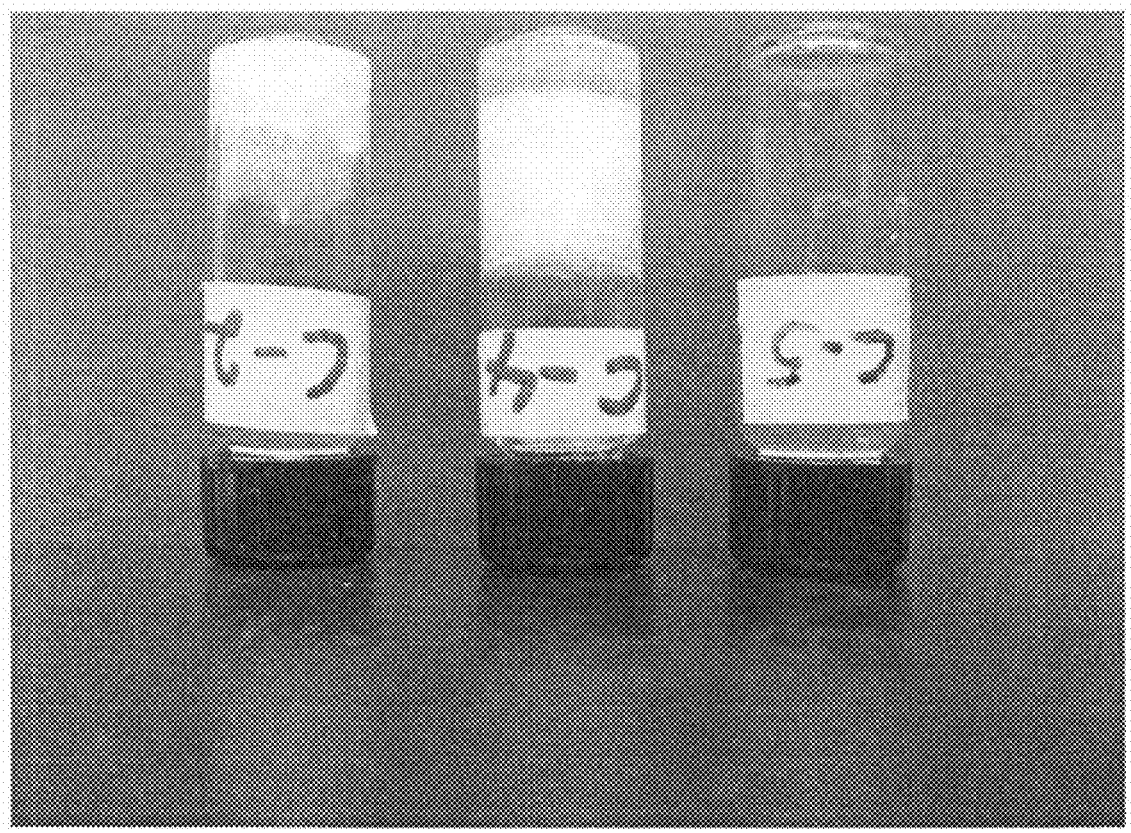
FIG. 18 is a pictorial representation showing the stability of hydrogels of 2% tetradecylmaltoside and 2% sucrose stearate/distearate to inversion. Sample C-2 is a hydrogel of 2% tetradecylmaltoside. Sample C-4 is a hydrogel of 2% sucrose stearate/distearate. Sample C-5 is water.
Figure 19:
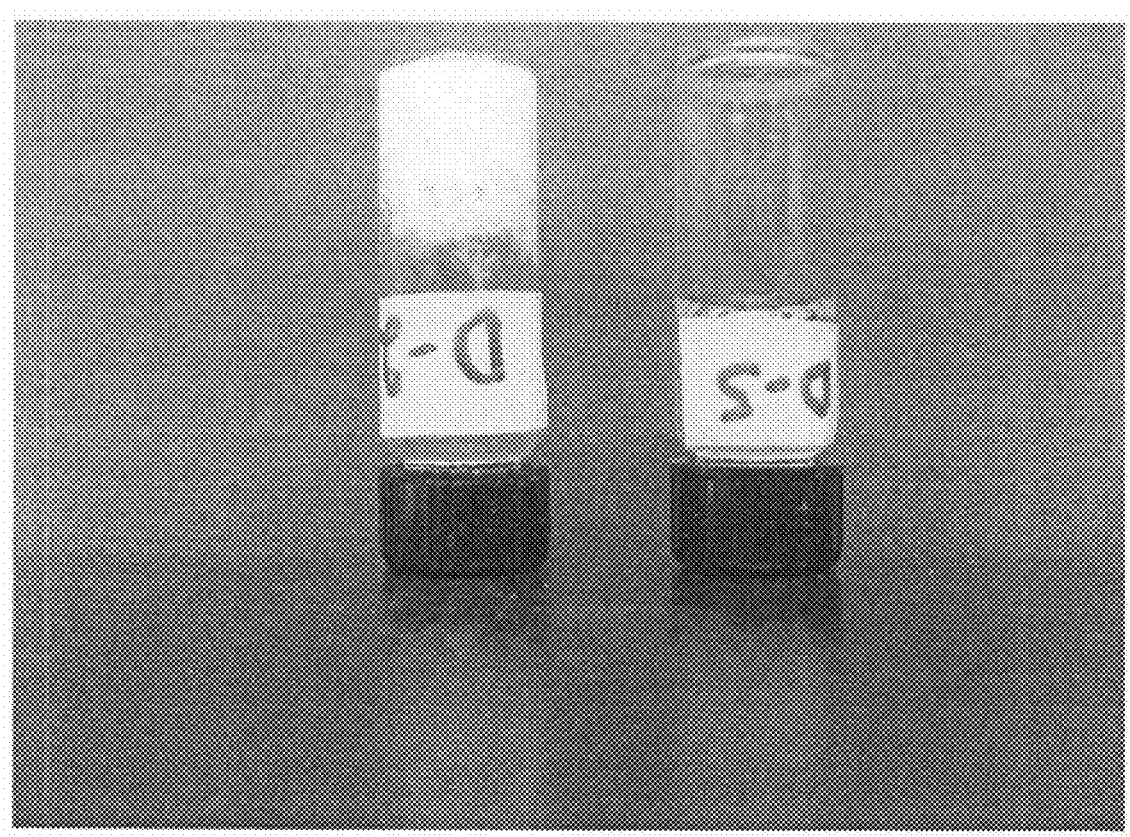
FIG. 19 is a pictorial representation showing the stability of hydrogels of 2% tetradecylmaltoside in 0.1 M sodium bicarbonate to inversion. Sample D-2 is a hydrogel containing 2% tetradecylmaltoside in 0.1 M sodium bicarbonate. Sample D-5 is a solution of 0.1 M sodium bicarbonate.

As discussed above it was also determined that alkylglycosides, such as tetradecylmaltoside have unique characteristics which make them capable of self-assembling into a hydrogel into which an active agent may be incorporated, such as curcumin, folic acid or methotrexate. FIG. 14 shows hydrogels of tetradecylmaltoside which self-assemble at room temperature and are stable to inversion. In the absence of a drug the tetradecylmaltoside forms a fibrous white matrix which entraps much of the water in the vial (C-2). When 2.5 mg/ml of folic acid is present in the solution the hydrogel encapsulates the compound as can be seen by the yellow color of the gel (A-2). For comparison a vial containing 2.5 mg/ml folic acid in water gives a clear solution with a thin sediment of insoluble folic acid at the bottom (A-5). Folic acid is poorly soluble in water but can be solubilized in slightly alkaline solutions e.g. in the presence of sodium bicarbonate. FIG. 15 shows hydrogels of tetradecylmaltoside identical to those shown in FIG. 14, but formulated in solutions containing 0.1 M sodium bicarbonate to solubilize the folic acid. Note the uniformly yellow color of the hydrogel containing 2.5 mg/ml folic acid in 0.1 M sodium bicarbonate (B-2) while the hydrogel formed in 0.1 M sodium bicarbonate with tetradecylmaltoside alone gives a white fibrous matrix (D-2). Folic acid gives a clear yellow solution in 0.1 M sodium bicarbonate (B-5). All of the hydrogels of 2% tetradecylmaltoside are stable to inversion at room temperature (see FIGS. 16-19).

Hydrogels which are stable to inversion can also self-assemble from solutions of sucrose esters of long chain fatty acids. Sucrose stearate/distearate (2%) forms a white gelatinous mass floating on a clear solution when left at room temperature (25 degrees C.) for 48-72 hours. The mass was a hydrogel which was stable to inversion (C-4 in FIG. 18).

Figure 20:
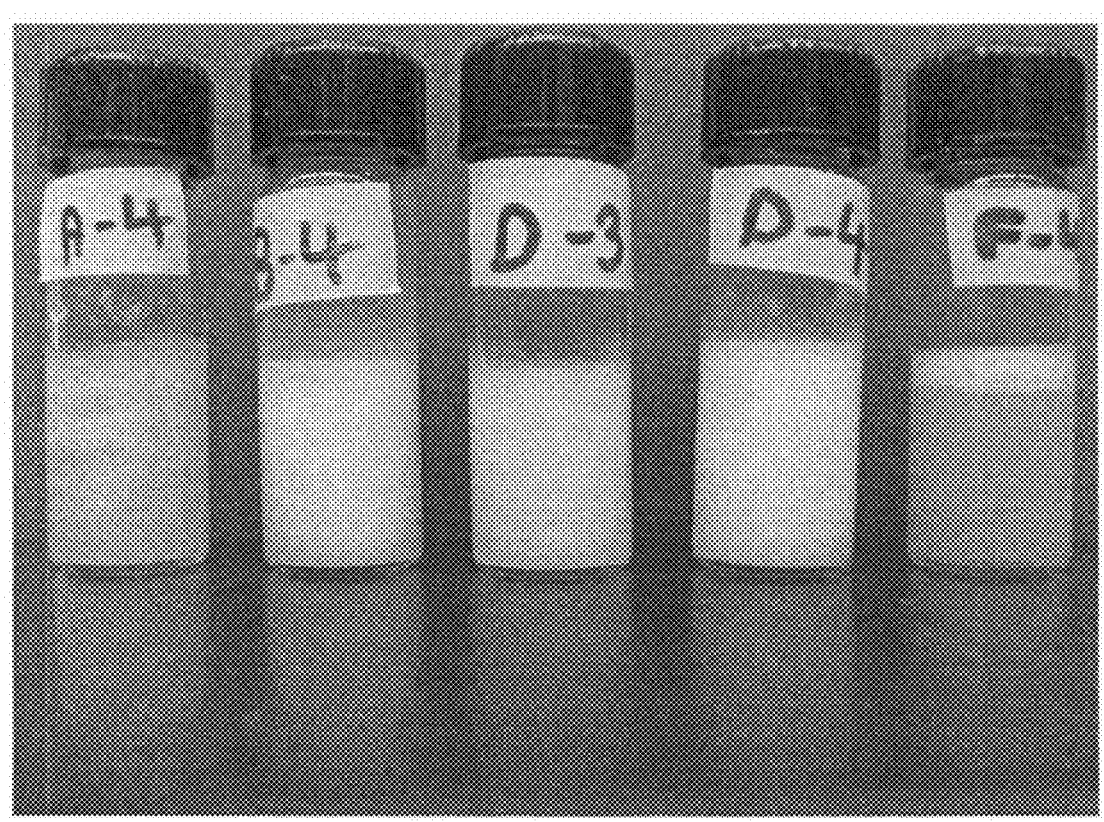
FIG. 20 is a pictorial representation showing hydrogels of sucrose esters of fatty acids. Sample A-4 is a hydrogel of 2% sucrose stearate/distearate containing 2.5 mg/ml folic acid. Sample B-4 is a hydrogel of 2% sucrose stearate in 0.1 M sodium bicarbonate containing 2.5 mg/ml folic acid. Sample D-3 is a hydrogel of 2% sucrose stearate in 0.1 M sodium bicarbonate. Sample D-4 is a hydrogel of 2% sucrose stearate/distearate in 0.1 M sodium bicarbonate. Sample F-4 is a hydrogel of 2% sucrose stearate/distearate in 0.1 M sodium bicarbonate containing 1 mM curcumin.
Figure 21:
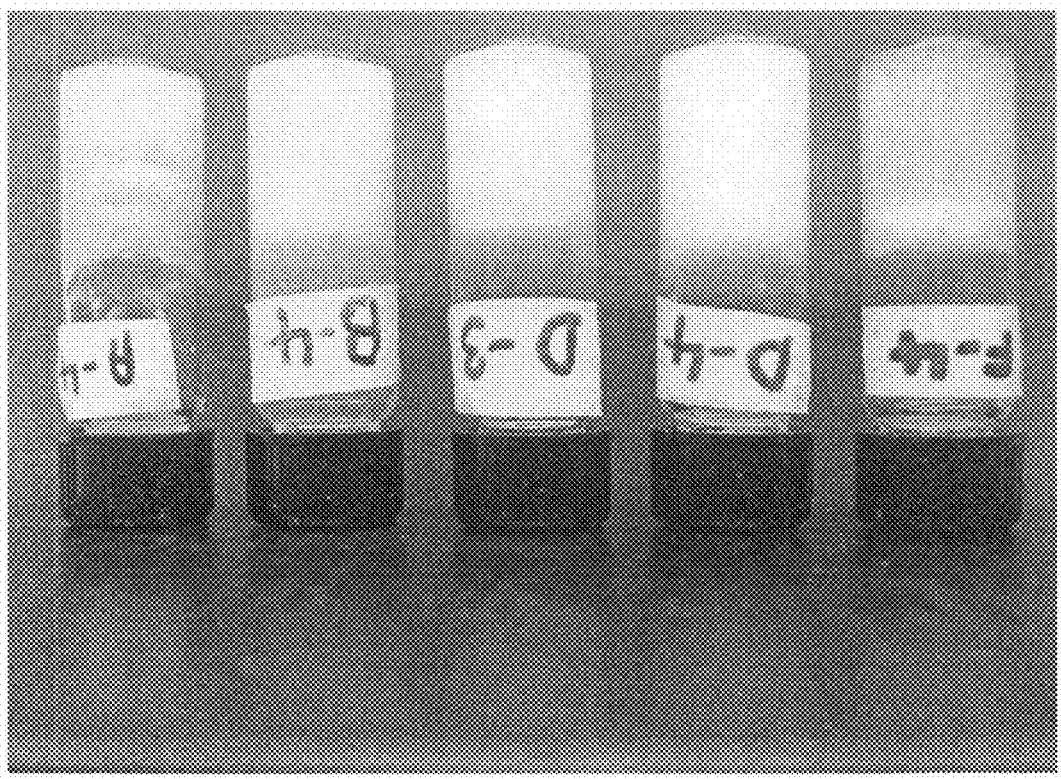
FIG. 21 is a pictorial representation showing stability of hydrogels of sucrose esters of fatty acids to inversion. The hydrogels are those shown in FIG. 20. All are firm gels which do not flow upon inversion.

Sucrose esters of fatty acids form stable invertible hydrogels under several different conditions either in the absence of any drug or in the presence of several different drugs. FIGS. 20 and 21 show several examples of these hydrogels. A-4 is a hydrogel of 2% sucrose stearate/sucrose distearate containing 2.5 mg/ml of folic acid. After several days at room temperature a gelatinous mass forms which is not stable to inversion. Heating this mass to 45 degrees C. for 30 minutes followed by vortexing and cooling to room temperature converts this mass into a stable invertible hydrogel with the yellow folic acid distributed throughout the gel. B-4 is a comparable hydrogel of 2% sucrose stearate/distearate containing 2.5 mg/ml of folic acid in 0.1 M sodium bicarbonate which is formed under similar conditions to A-4. Folic acid completely dissolves in 0.1 M sodium bicarbonate giving a clear light yellow solution accounting for the uniform distribution of the compound in the hydrogel. D-3 and D-4 are hydrogels without drug formed under comparable conditions from 2% sucrose stearate and 2% sucrose stearate/sucrose distearate respectively both in 0.1 M sodium bicarbonate. F-4 is a similar hydrogel containing 1 mM curcumin formed from 2% sucrose stearate/sucrose distearate in 0.1 M sodium bicarbonate again after heating to 45 degrees C., vortexing to distribute the curcumin and letting the hydrogel form upon cooling to room temperature.

Figure 22:
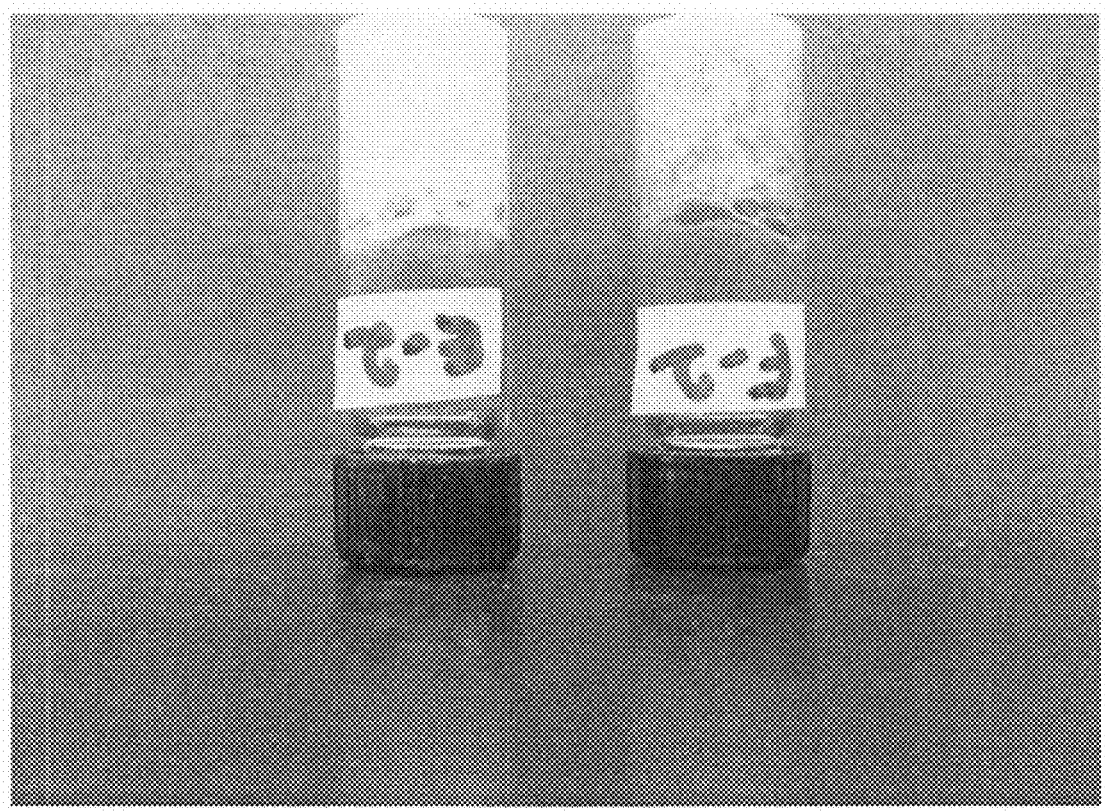
FIG. 22 is a pictorial representation showing the stability of hydrogels of curcumin in tetradecylmaltoside to inversion. The hydrogels those shown in FIG. 13. Sample E-2 is a hydrogel composed of 2% tetradecylmaltoside and 1 mM curcumin. Sample F-2 is a hydrogel composed of 2% tetradecylmaltoside, 1 mM curcumin, and 0.1 M sodium bicarbonate.

The hydrogels of 1 mM curcumin in 2% tetradecylmaltoside which self-assemble at room temperature without any heating (FIG. 13) are also stable to inversion (FIG. 22), In general while hydrogels formed from 2% tetradecylmaltoside self-assemble at room temperature and dissolve at 37 degrees C. releasing any drug contained within the matrix of the gel, those formed from 2% sucrose stearate or 2% sucrose stearate/sucrose distearate require heating of the gelator or gelator/drug mixture to 37-45 degrees C. followed by vortexing of the mixture and cooling to room temperature in order to form stable gels.

Figure 23:
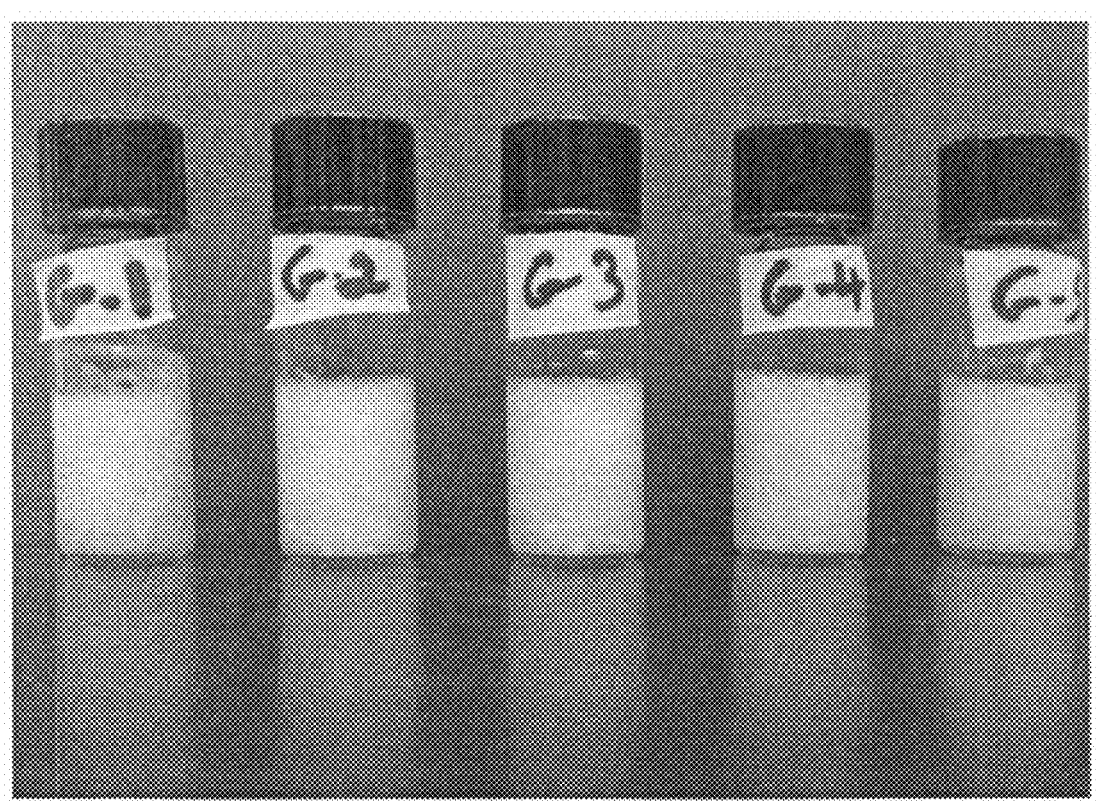
FIG. 23 is a pictorial representation showing the reproducibility of formation of hydrogels of tetradecylmaltoside containing folic acid. Samples G-1 to G-5 are five identical hydrogels of 2% tetradecylmaltoside containing 2.5 mg/ml folic acid.
Figure 24:
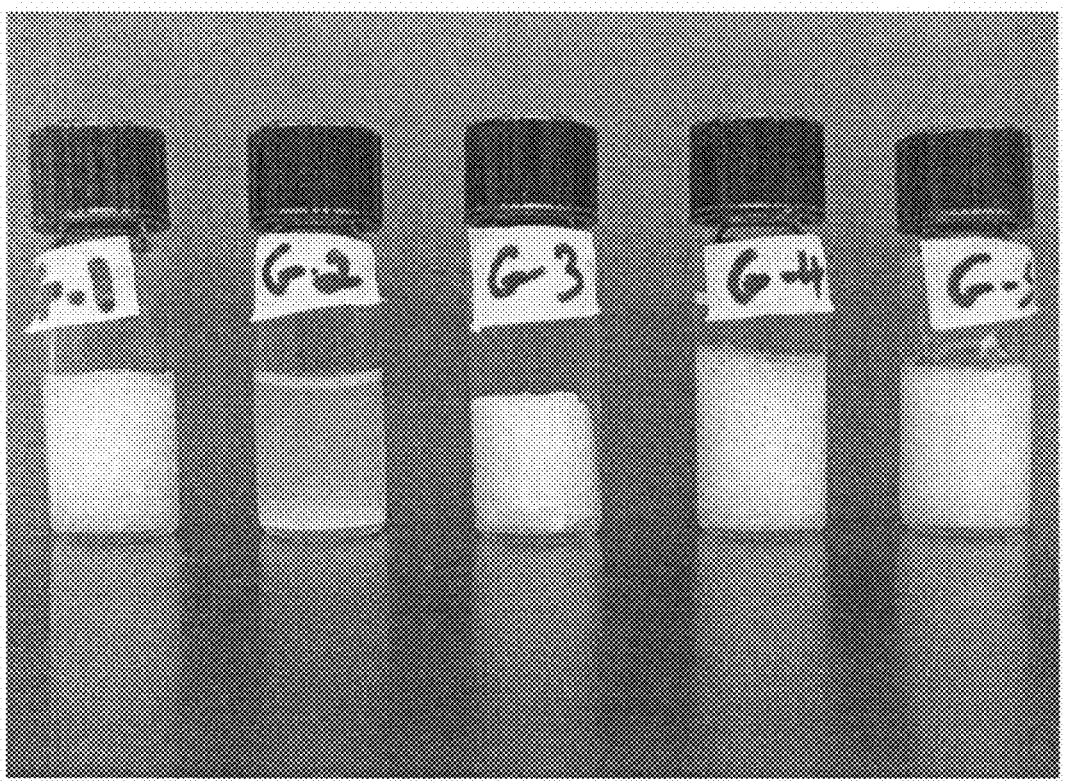
FIG. 24 is a pictorial representation showing the sensitivity of hydrogels of tetradecylmaltoside containing folic acid to temperature and enzyme treatment. The hydrogels are those shown in FIG. 23. Samples G-1 and G-5 were untreated. Sample G-2 was heated to 37 degrees C. for 1 hour. Sample G-3 was treated with amyloglucosidase in acetate buffer while sample G-4 was treated with buffer alone without mixing.

To determine the sensitivity of hydrogels of 2% tetradecylmaltoside containing 2.5 mg/ml folic acid to temperature and enzymatic treatment five identical gels were formed by self-assembly over several days into a uniform yellow fibrous gel matrix (FIG. 23). The reproducibility of the self-assembly is evidenced by the almost identical appearance of the five samples G-1 to G-5. The hydrogels formed at room temperature over several days without heating or other treatment and were stable to inversion. G-1 was left untreated and was stable indefinitely at room temperature. At room temperature the folic acid was evenly distributed throughout the gel. G-2 was heated to 37 degrees C. for 1 hour. After 5 minutes of heating the gel liquefied to an opaque mixture and became clearer and more fluid as the heating continued (FIG. 24). The liquefying of the hydrogel was irreversible and the gel did not reform on cooling. When a solution containing 1 mg of amyloglucosidase in 0.5 ml of sodium acetate buffer, pH 5.0, was pipetted on top of the gel and left to stand at room temperature for several days some erosion at the top and sides of the gel was seen compared to an identical gel which was exposed to the buffer solution alone (G-3 vs. G-4 in FIG. 24). The maltose moiety of tetradecylmaltoside is susceptible to cleavage by amyloglucosidase. There was little or no diffusion of the yellow folic acid into the supernatant solution indicating that it was retained within the gel matrix as long as the gel remained intact.

Figure 25:
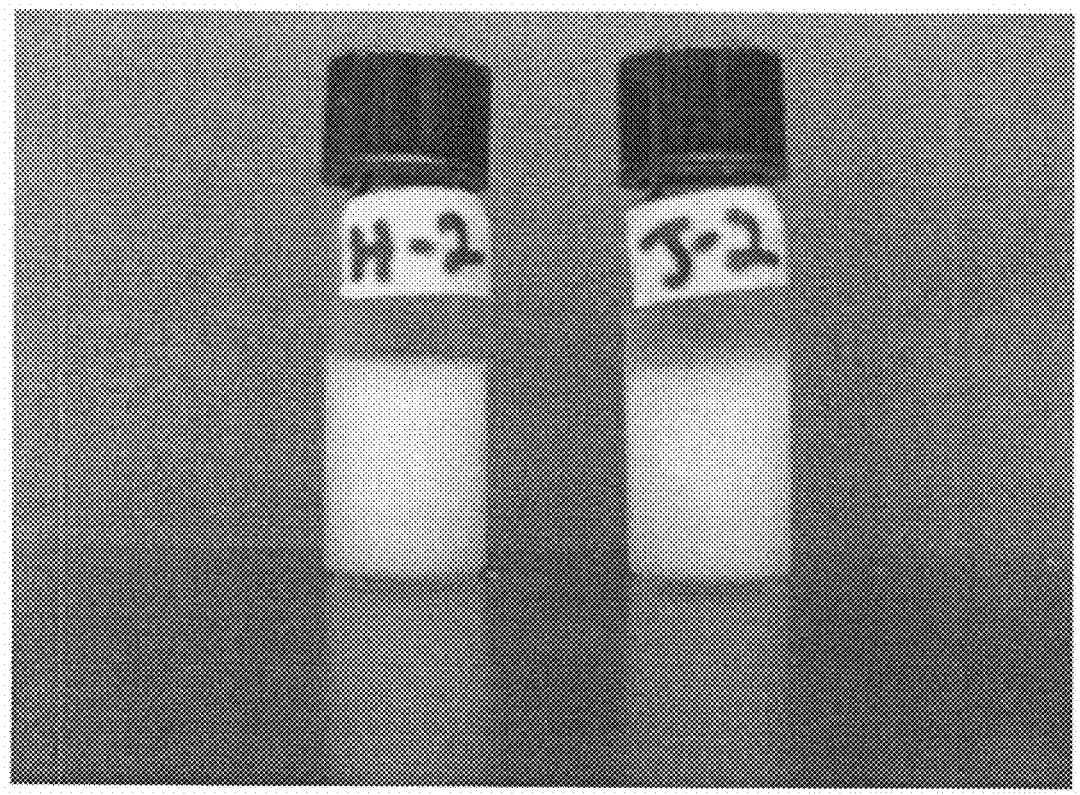
FIG. 25 is a pictorial representation showing hydrogels of sucrose stearate/distearate containing folic acid. Samples H-2 and J-2 are hydrogels of 2% sucrose stearate/distearate containing 2.5 mg/ml folic acid in the absence (sample H-2) and presence (sample J-2) of 0.1 M sodium bicarbonate.
Figure 26:
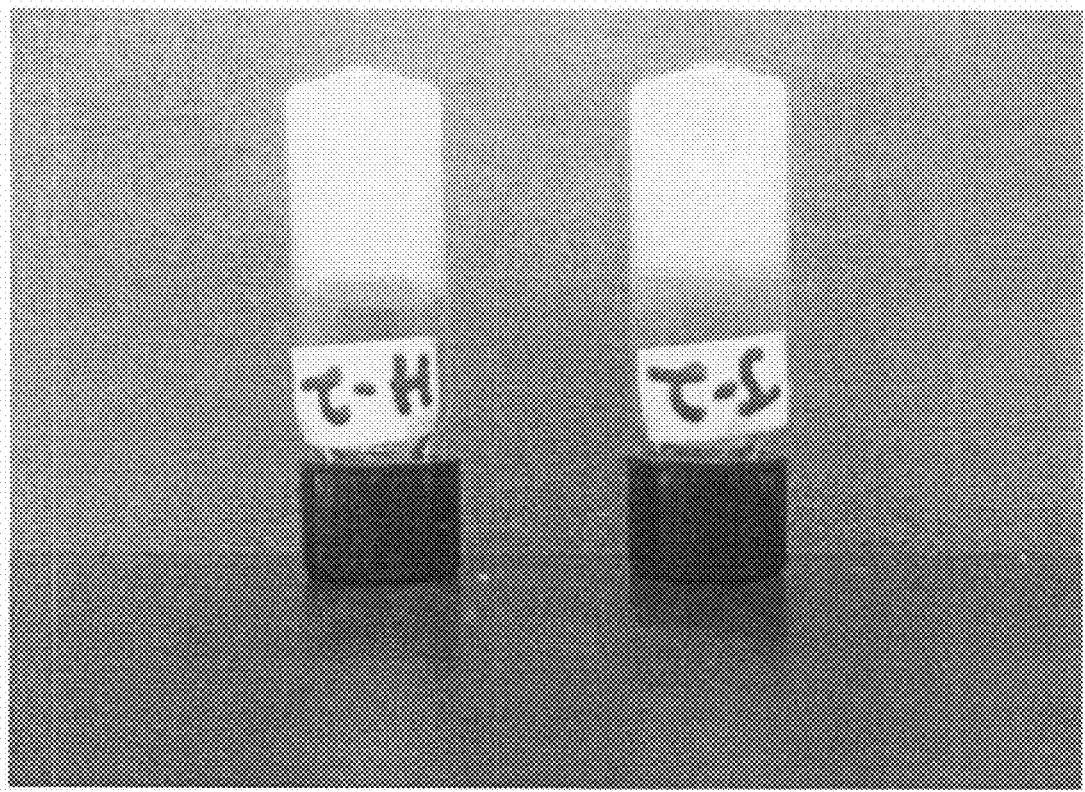
FIG. 26 is a pictorial representation showing the stability to inversion of hydrogels of sucrose stearate/distearate containing folic acid. The hydrogels are those shown in FIG. 25.
Figure 27:
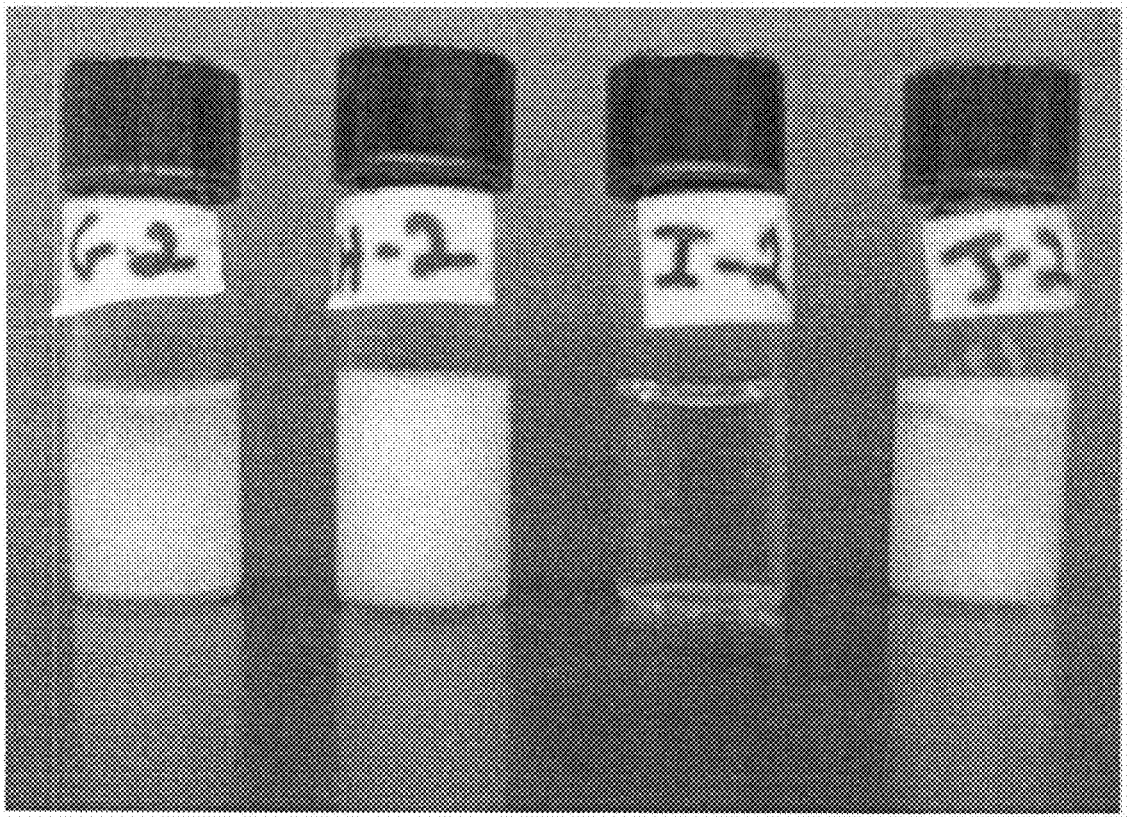
FIG. 27 is a pictorial representation showing the stability of hydrogels of tetradecylmaltoside and sucrose stearate/distearate to temperature. Samples G-2 and 1-2 are hydrogels of 2% tetradecylmaltoside containing 2.5 mg/ml folic acid in the absence (sample G-2) and presence (sample 1-2) of 0.1 M sodium bicarbonate after heating to 37 degrees C. for 1 hour. Samples H-2 and J-2 are hydrogels formed of 2% sucrose stearate/distearate containing 2.5 mg/ml folic acid in the absence (sample H-2) and presence (sample J-2) of 0.1 M sodium bicarbonate after heating to 37 degrees C. for 1 hour.

In contrast to hydrogels of 2% tetradecylmaltoside which self-assemble at room temperature into stable invertible gels which trap the surrounding solvent and any drug dissolved or suspended in it, hydrogels of 2% sucrose stearate/sucrose distearate do not form at room temperature, but only after being heated to 37-45 degrees C., mixing by vortexing to distribute the solvent and drug uniformly, and then allowing the mixture to cool to room temperature. Examples of such hydrogels in which 2.5 mg/ml of folic acid is uniformly distributed in the gel in the absence and presence of 0.1 M sodium bicarbonate are shown in FIG. 25 (H-2 and J-2 respectively). These gels are stable to inversion (FIG. 26) and soften, but do not liquefy when reheated to 37 degrees C. The contrasting sensitivity to temperature of hydrogels of 2% tetradecylmaltoside and 2% sucrose stearate/sucrose distearate all containing 2.5 mg/ml folic acid is summarized in FIG. 27.

Figure 28:
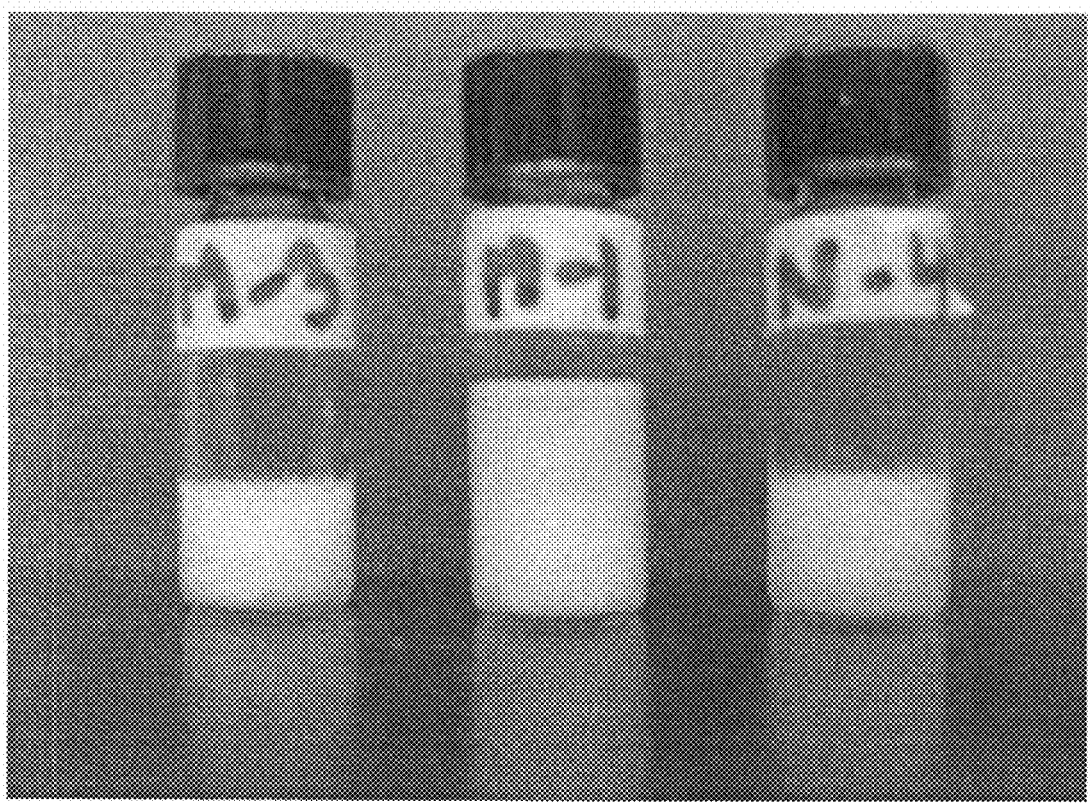
FIG. 28 is a pictorial representation showing hydrogels of folate and methotrexate. Sample M-3 is a hydrogel composed of 2% tetradecylmaltoside and 2.5 mg/ml methotrexate. Sample N-4 is a hydrogel composed of 2% sucrose stearate/distearate and 2.5 mg/ml folic acid. Sample M-1 is a bilayer hydrogel composed of 2% tetradecylmaltoside/2.5 mg/ml methotrexate in the bottom layer and 2% sucrose stearate/distearate/2.5 mg/ml folic acid in the top layer.
Figure 29:
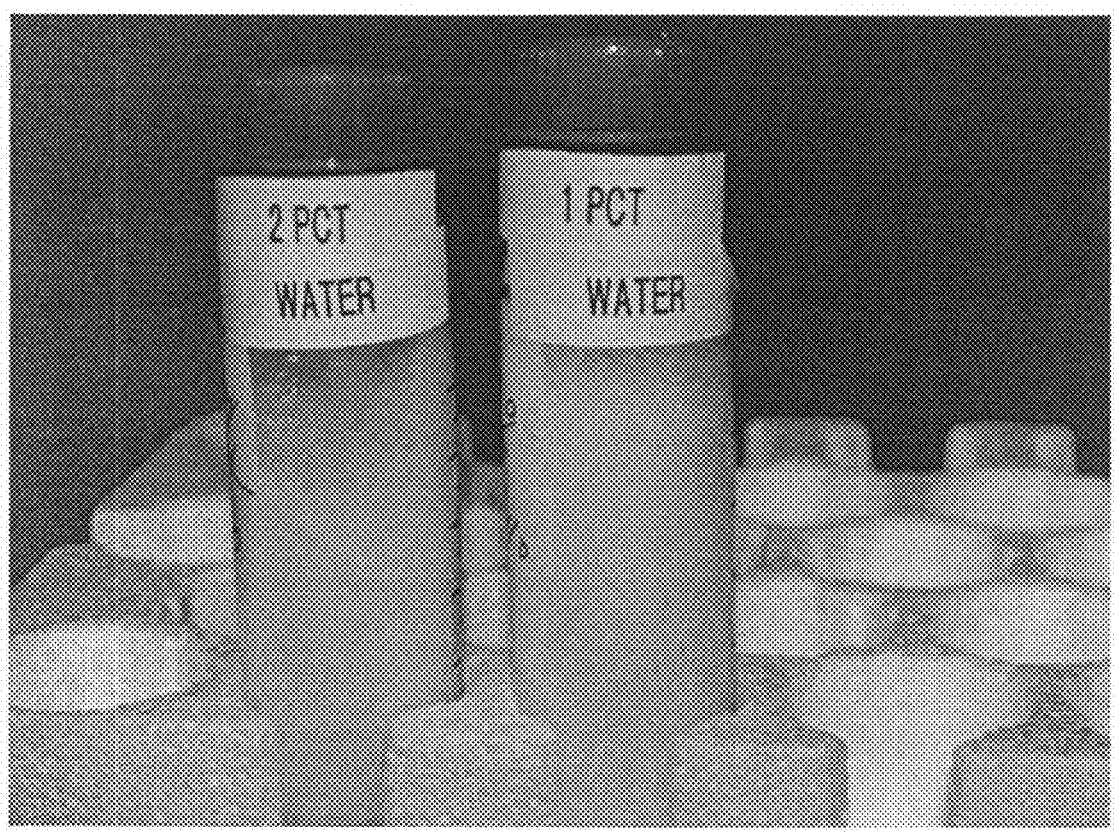
FIG. 29 is a pictorial representation showing the stability of hydrogels which include water and INTRAVAIL B9® at 1% and 2% concentration.
Figure 30:
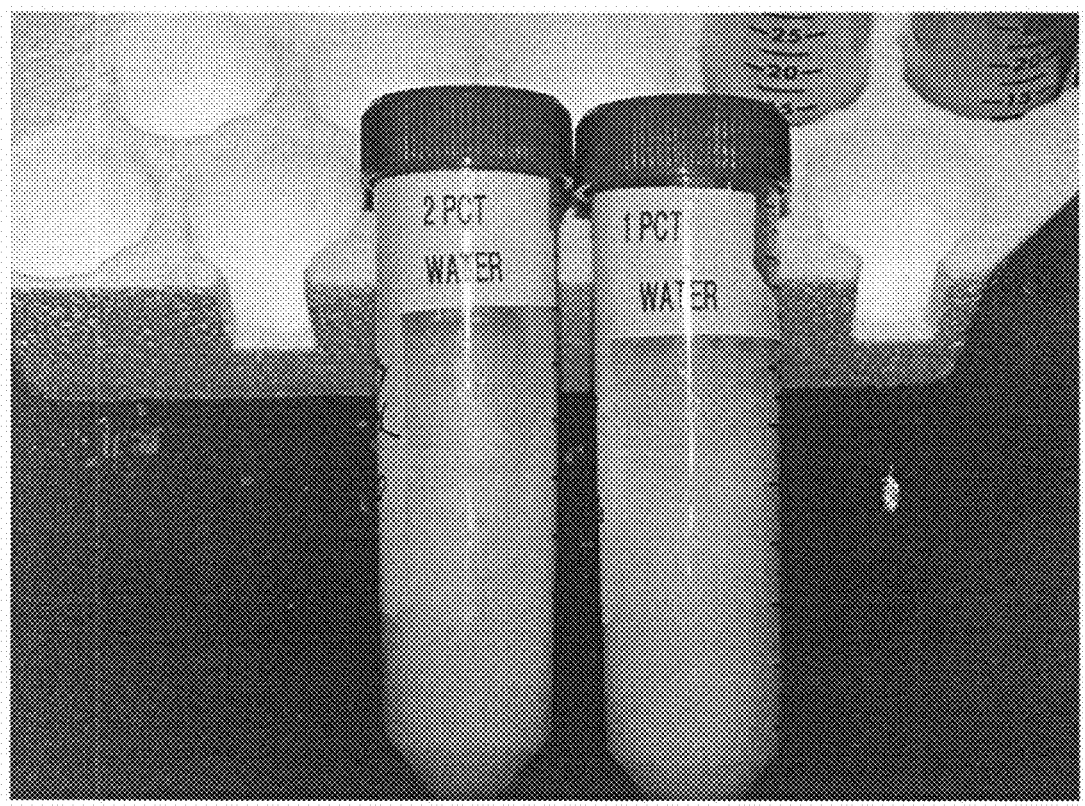
FIG. 30 is a pictorial representation showing the stability of hydrogels which include water and INTRAVAIL B9® at 1% and 2% concentration.
Figure 31:
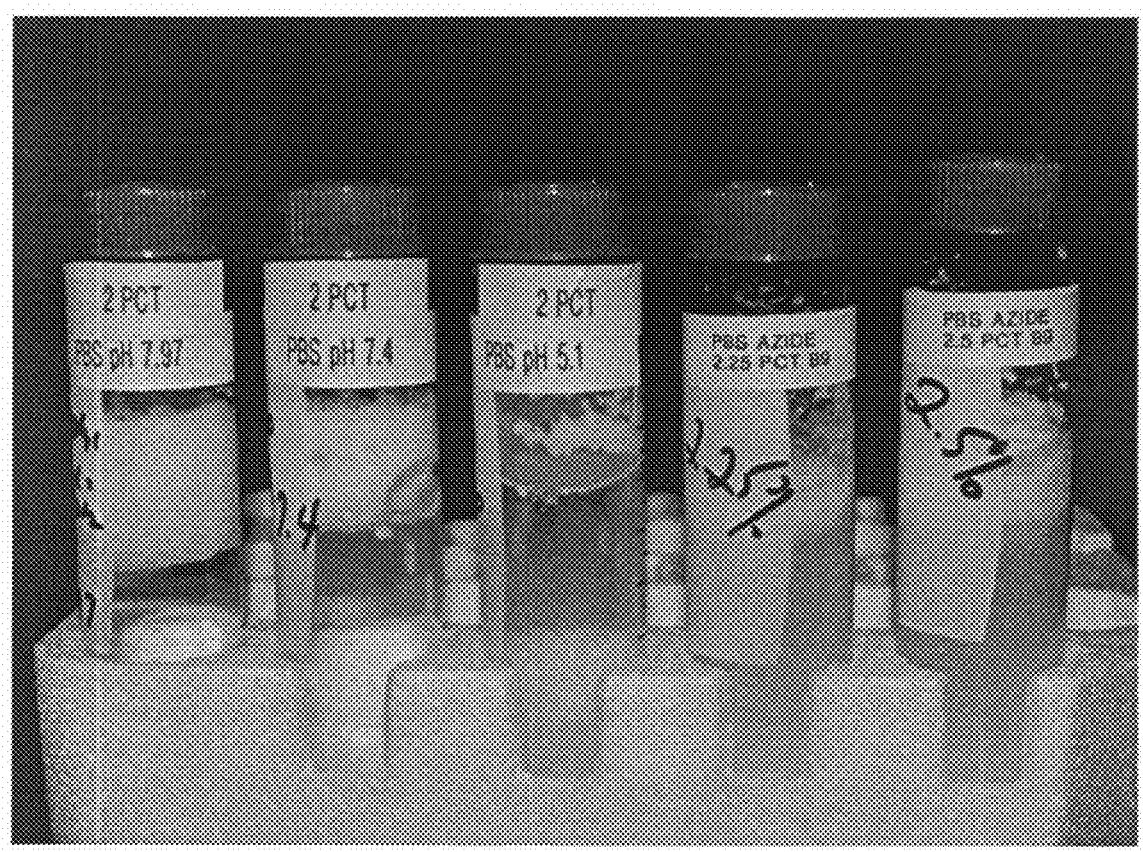
FIG. 31 is a pictorial representation showing the stability of hydrogels which include PBS: INTRAVAIL B9® at 2% (pH 7.97, 7.4, 5.1) and 2.25% PBS (pH 7.4) with sodium azide added.
Figure 32:
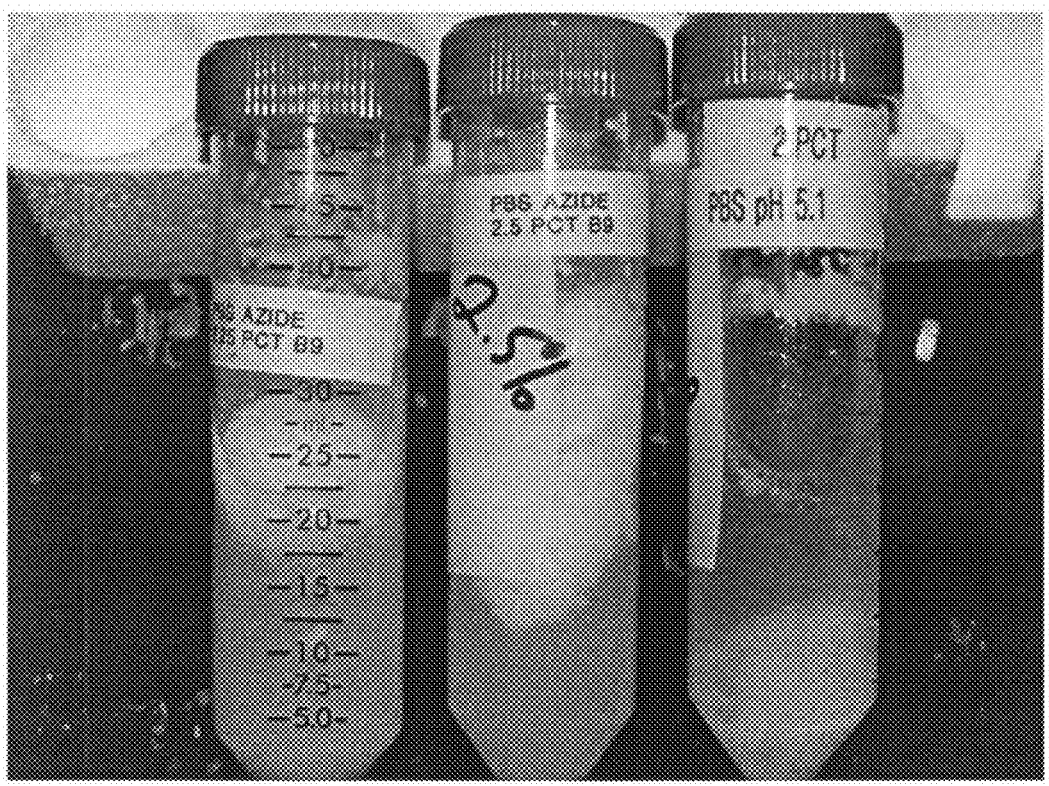
FIG. 32 is a pictorial representation showing stability of hydrogels which include PBS: INTRAVAIL B9® at pH 7.4 at 2.25% and 2.5% with sodium azide added and PBS (pH 5.1) at 2% INTRAVAIL B9®.
Figure 33:
FIG. 33 is a pictorial representation showing stability of hydrogels which include PBS: INTRAVAIL B9® at 2% (pH 7.97, 7.4).
Figure 34:
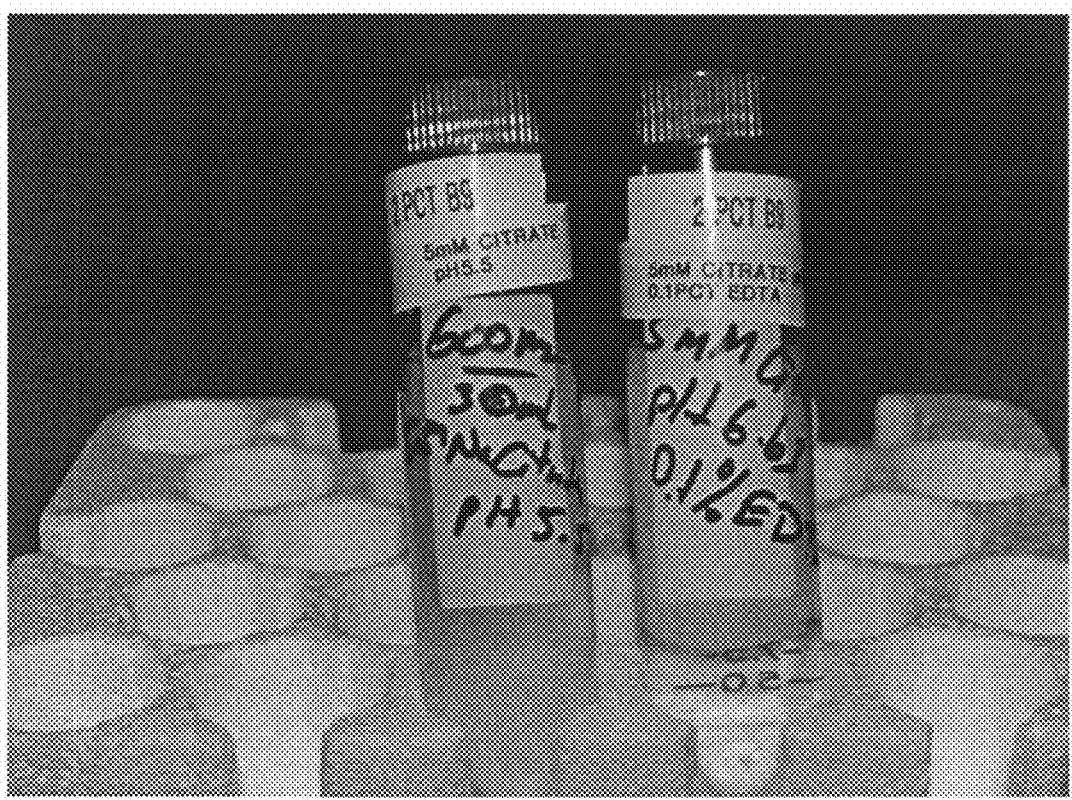
FIG. 34 is a pictorial representation showing stability of hydrogels which include 5 mM citrate: INTRAVAIL B9® at 2% (pH 5.5) and 6.63 with 0.1% EDTA added.
Figure 35:
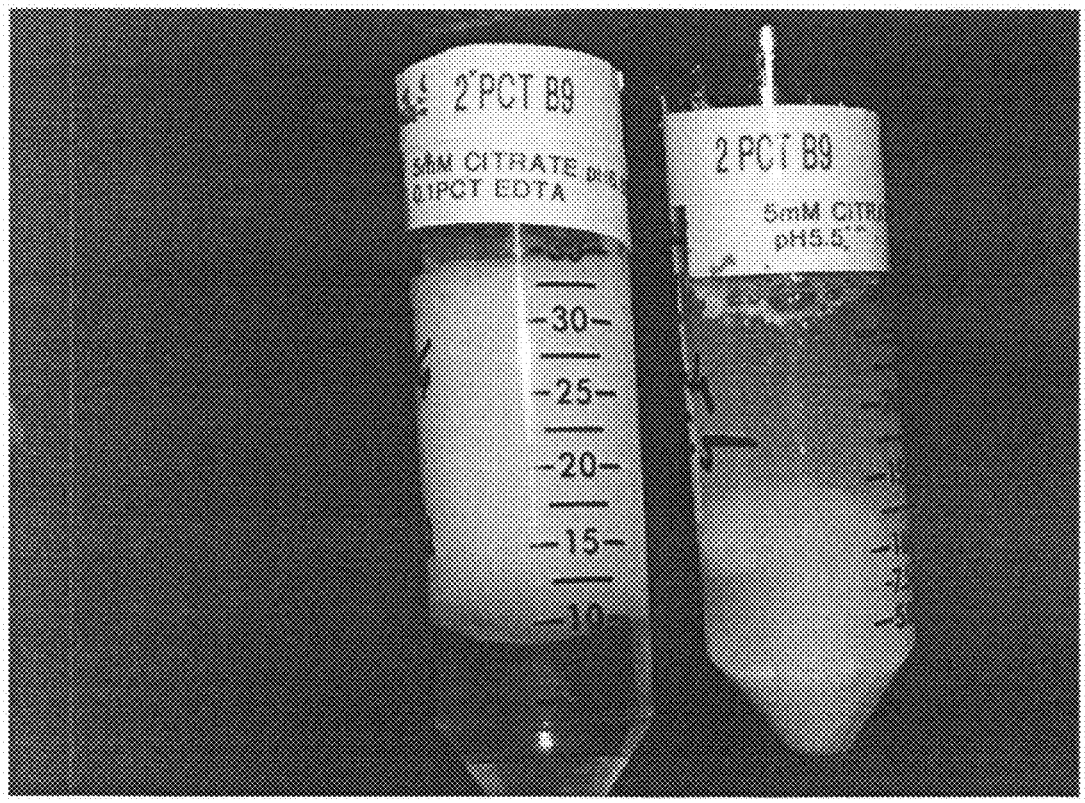
FIG. 35 is a pictorial representation showing stability of hydrogels which include citrate: INTRAVAIL B9® at 2% (pH 5.5 and 6.63 with 0.1% EDTA added.
Figure 36:
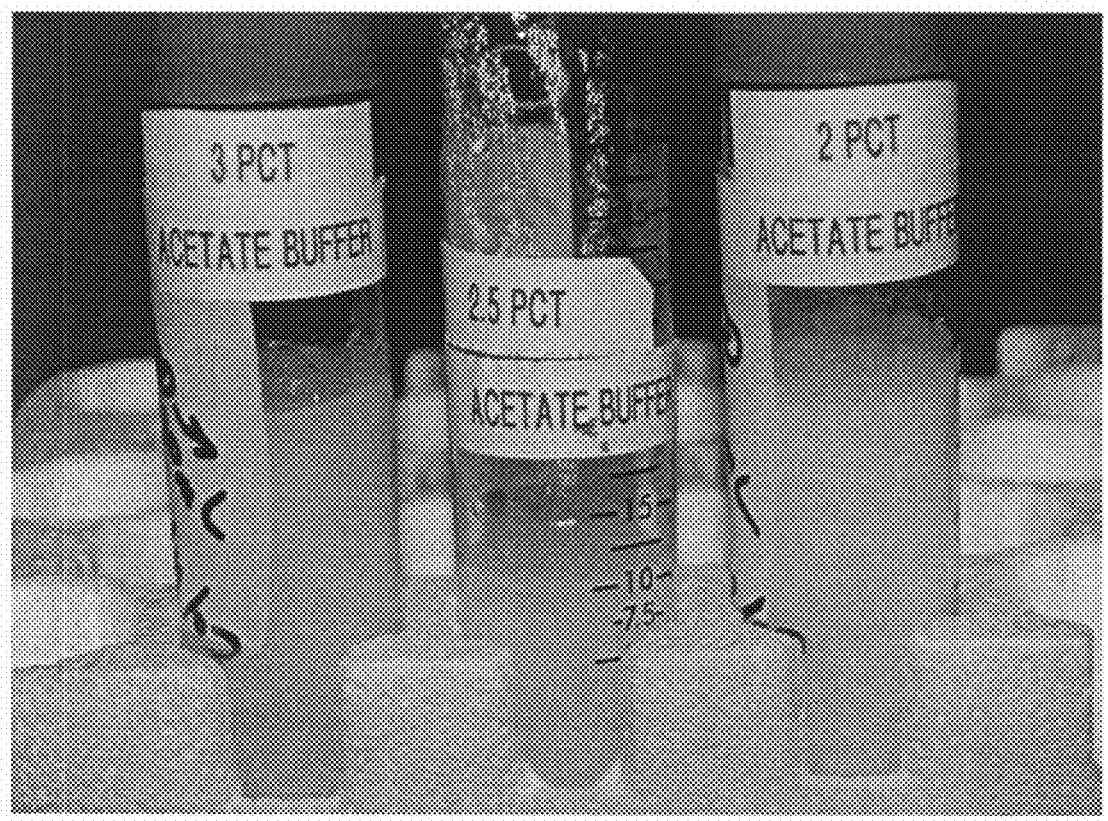
FIG. 36 is a pictorial representation showing stability of hydrogels which include 10 mM acetate: INTRAVAIL B9® at 3%, 2.5%, and 2% (pH 5.5).
Figure 37:
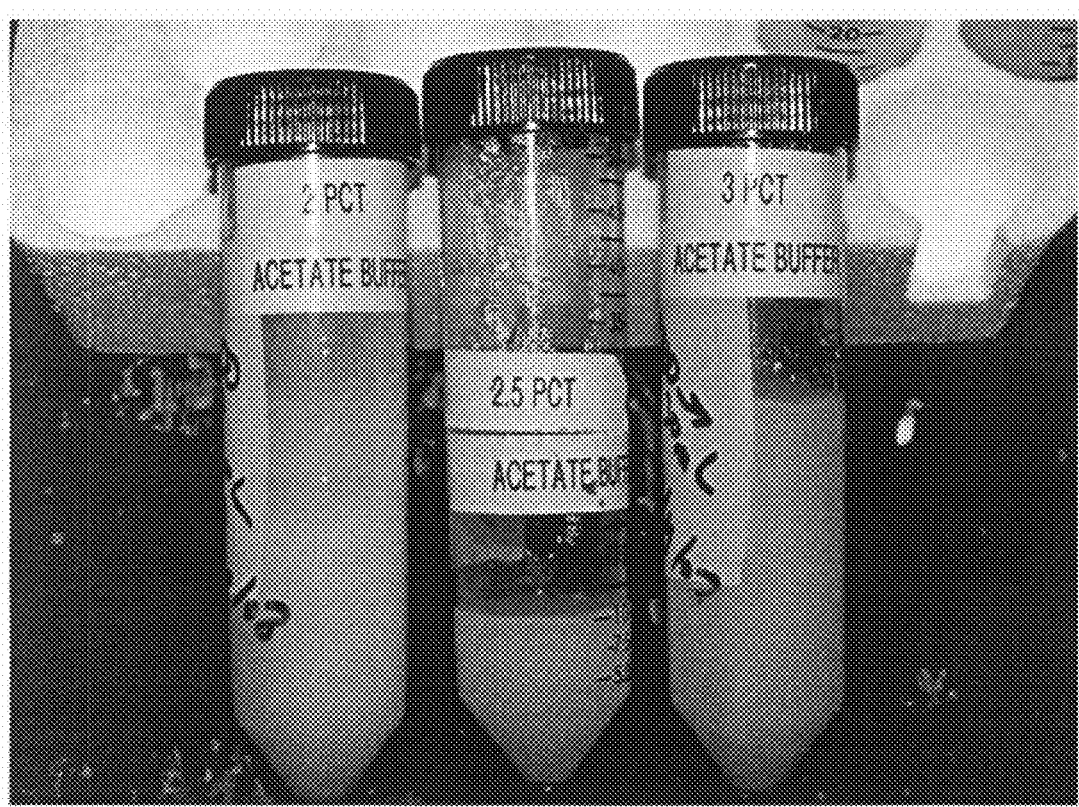
FIG. 37 is a pictorial representation showing stability of hydrogels which include acetate: INTRAVAIL B9® at 3%, 2.5%, and 2% (pH 5.5).

The differential sensitivity to temperature of hydrogels of 2% tetradecylmaltoside and 2% sucrose stearate/sucrose distearate can be exploited to encapsulate different drugs and to allow them to be released and absorbed at different times due to the different properties of the hydrogels. For example, bilayer hydrogels containing both folic acid and methotrexate could be prepared. FIG. 28 shows such a hydrogel in which 2% tetradecylmaltoside/2.5 mg/ml methotrexate comprises the bottom layer of the gel and 2% sucrose stearate/distearate containing 2.5 mg/ml folic acid comprises the top layer. A composite gel of this type containing two different compounds in two hydrogelators of different properties would allow differential release of the compounds encapsulated in the gel by exploiting the differences in thermolability and enzyme sensitivity of the hydrogelators. For example the bilayer hydrogel shown in FIG. 16 would release the encapsulated methotrexate rapidly due to the liquefication of the tetradecylmaltoside layer at the body temperature of 37 degrees C., while a delayed release of the folic acid from the sucrose monostearate/distearate layer would occur, since this layer is thermostable at 37 degrees C., but would be susceptible to enzymatic degradation of the gelator by esterases and lipases present in the gastrointestinal tract. This bilayer gel was created by first forming the tetradecylmaltoside/methotrexate hydrogel at 25 degrees C. and then layering a suspension of folic acid in sucrose monostearate/distearate, which had been heated to 37 degrees and allowed to cool, on top of the gelled tetradecylmaltoside layer and allowing it to gel.

Example 2

Preparation of Hydrogels Including Acetate Buffered Gels

Stability of hydrogels that include acetate as the buffer was determined by preparation of gel compositions as shown in Table 1. A number of pH's and concentrations of sucrose stearate and distearate (INTRAVAIL B9®, known as CRODESTA F-110). FIGS. 29-37 show photographs of the tubes at 120 days after storage at room temperature. The acetate buffered gels continue to be completely stable after 120 days at room temperature.

TABLE 1

Key to Photographs of Hydrogels of FIGS. 29-37

| Tube | Conc. | pH | Buffer | Intravail B9** Conc. | Additional Components |
|---|---|---|---|---|---|
| A |  | neutral | Water | 1% | none |
| B |  | neutral | Water | 2% | none |
| C | Std. | 7.97 | PBS* | 2% | Na+ Azide |
| D | Std. | 7.4 | PBS | 2% | Na+ Azide |
| E | Std. | 5.1 | PBS | 2% | Na+ Azide |
| F | Std. | 7.4 | PBS | 2.25% | Na+ Azide |
| G | Std. | 7.4 | PBS | 2.50% | Na+ Azide |
| H | 5 mM | 5.5 | Citrate | 2% | 0.1% EDTA |
| I | 5 mM | 6.63 | Citrate | 2% | 0.1% EDTA |
| J | 10 mM | 5.5 | Acetate | 3% | none |
| K | 10 mM | 5.5 | Acetate | 2.50% | none |
| L | 10 mM | 5.5 | Acetate | 2% | none |

*Phosphate Buffered Saline
**Intravail B9 = CRODESTA F-110 ® (Sucrose stearate and distearate) Croda Inc.

Example 3

Administration of Acetate Buffered Hydrogels Including Methotrexate for Treatment of Arthritis Methotrexate is classified as a first choice for rheumatoid arthritis treatment in Europe, America, Japan and many other countries. Nonetheless, methotrexate is well known to induce various problems such as leukopenia and thrombocytopenia, hepatic problems, gastrointestinal ulcer, diarrhea, mucosal erosion, erythema and alopecia. Development of serious side effects such as bone marrow failure and interstitial pneumonia his arisen as an especially serious problem. Methotrexate has also been found to be effective in treatment of psoriasis. Administration of this drug to patients has conventionally been performed orally, for example, in the form of tablets or capsules. Oral administration is, however, accompanied by the problem of the first-pass effect at the liver in that upon passage through the liver, a drug is substantially metabolized there before it reaches an affected part. Further, methotrexate has a potential problem of development of side effects as mentioned above although its drug efficacy is strong. For its use, an utmost care is therefore needed. Under these circumstances, methotrexate is used only when an advantage which would be available from its administration is judged to surpass the risk of development of side effects. Accordingly, hydrogels as described herein including methotrexate may be administered nasally to avoid the first pass effect of the liver.

The methotrexate-containing hydrogel preparation in acetate buffer described herein, when administered dermally, proximal to the affect joint or psoriatic lesion, permits local absorption of the drug into the affected area. This may be demonstrated using a percutaneous absorption test. In this test, Wistar strain rats, seven weeks old, weighing approximately 200 to 250 g, are shaved using a hair clipper on the dorsal portion of the back. A fixed amount (for example, 100 μL) of methotrexate-containing aqueous hydrogel (3% methotrexate) is applied to the shaved skin in an area of approximately 1-2 cm$^2$. A blood sample is collected immediately prior to administration of the hydrogel and at intervals of one, two, four, and eight hours and blood concentrations of methotrexate are measured. At lower concentrations of methotrexate in the hydrogel, the drug is distributed substantially locally. At higher concentrations of drug in the hydrogel, absorption into systemic circulation blood can be increased thus providing systemic administration, while avoiding the first pass effect in the liver. Topical local administration of the methotrexate containing hydrogel permits smaller total doses of methotrexate to be administered. Thus providing effective treatment of rheumatoid arthritis in affected joints with reduced total patient exposure of drug and therefore reduced likelihood of unwanted side effects.

In various embodiments, the proportion of methotrexate may range from about 0.1 to 10 wt. %, preferably from 1 to 5 wt. %. In an exemplary embodiment, the proportion of methotrexate is 3 wt. %.

What is claimed is:
1. A buffered hydrogel comprising:
   a) a therapeutic agent;
   b) a sucrose ester, wherein the sucrose ester is a combination of sucrose stearate and sucrose distearate; and
   c) a buffer,
   wherein the hydrogel is formed by heat treatment of a suspension of (a)-(c) at temperatures of 37-45° C.
2. The hydrogel of claim 1, further comprising a preservative.
3. The hydrogel of claim 2, wherein the preservative is ethylene diamine tetraacetic acid (EDTA), benzalkonium chloride, sodium azide or dodecyl maltoside.
4. The hydrogel of claim 1, wherein the hydrogel has a pH from 4 to 8.
5. The hydrogel of claim 1, wherein the hydrogel has a pH from 4.5 to 6.5.

6. The hydrogel of claim 1, wherein the therapeutic agent is a peptide, hormone, steroid, anti-inflammatory, anti-biotic, anti-viral, UV blocker, or anti-wrinkle agent.

7. The hydrogel of claim 6, wherein the agent is an anti-wrinkle agent selected from the group consisting of: retinol, retinoic acid, 13-trans retinoic acid, 13-cis retinoic acid, retinyl ester, hydroxy acid, alpha hydroxy acid, beta hydroxy acid, poly hydroxy acid, glycolic acid, lactic acid, an exfoliant, a Coenzyme Q10 copper peptide, a kinetin, a tea extract, and a collagen.

8. The hydrogel of claim 6, wherein the steroid is testosterone.

9. The hydrogel of claim 6, wherein the peptide is thymosin β-4.

10. The hydrogel of claim 6, wherein the buffer is an acetate buffer.

11. The hydrogel of claim 6, wherein the buffer is a citrate buffer.

12. The hydrogel of claim 6, wherein the therapeutic agent is uniformly distributed throughout the hydrogel.

* * * * *